(12) United States Patent
Newman et al.

(10) Patent No.: US 9,060,728 B2
(45) Date of Patent: Jun. 23, 2015

(54) APPARATUS FOR HEALTH CORRELATION ASSESSMENT

(75) Inventors: Richard W. Newman, Auburn, NY (US); Min Xu, Cortland, NY (US); Jiejing Qiu, Syracuse, NY (US); Edward O'Neil, Weedsport, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 0 days.

(21) Appl. No.: 13/620,486

(22) Filed: Sep. 14, 2012

(65) Prior Publication Data

US 2013/0253367 A1    Sep. 26, 2013

Related U.S. Application Data

(60) Continuation-in-part of application No. 12/430,202, filed on Apr. 27, 2009, now abandoned, which is a continuation-in-part of application No. 12/794,053, filed on Jun. 4, 2010, now Pat. No. 8,439,501, which is (Continued)

(51) Int. Cl.
| | | |
|---|---|---|
| *A61B 3/00* | (2006.01) | |
| *A61B 5/16* | (2006.01) | |
| *A61B 3/113* | (2006.01) | |
| *A61B 3/12* | (2006.01) | |

(Continued)

(52) U.S. Cl.
CPC . *A61B 5/16* (2013.01); *A61B 3/022* (2013.01); *A61B 3/113* (2013.01); *A61B 3/1241* (2013.01); *A61B 5/14532* (2013.01)

(58) Field of Classification Search
USPC ........................................................ 600/558
See application file for complete search history.

(56) References Cited

U.S. PATENT DOCUMENTS

| 4,310,003 A | 1/1982 | Schlager |
| 4,428,382 A | 1/1984 | Walsall et al. |

(Continued)

FOREIGN PATENT DOCUMENTS

| DE | 19730503 | 1/1998 |
| EP | 0578908 | 1/1994 |

(Continued)

OTHER PUBLICATIONS

Risacher, S. et al., "The Visual Contrast Sensitivity in Alzheimer's Disease, Mild Cognitive Impairment, and Older Adults with Cognitive Complaints", Neurobiology of Aging, Oct. 19, 2012, http://dx.doi.org/10.1016/j.neurobiolaging.2012.08.007.

(Continued)

*Primary Examiner* — Unsu Jung
*Assistant Examiner* — Phong K Huynh
(74) *Attorney, Agent, or Firm* — Kenneth J. Lukacher Law Group; R. S. Rosenholm

(57) ABSTRACT

An apparatus, system and method for performing a health correlation assessment based upon results an eye contrast sensitivity measurement test of a person. The health correlation assessment yields a predictive and probabilistic measure of the likelihood of the person appropriately assigned to a particular clinical health classification. Such an eye contrast sensitivity measurement can be used to identify people who are likely to be within a pre-Alzheimer's disease state or within Alzheimer's disease state of health and identify those who should seek further clinical and/or other types of testing to ascertain their actual health status and to determine an appropriate course of medical treatment.

25 Claims, 20 Drawing Sheets

Related U.S. Application Data a continuation of application No. 12/505,193, filed on Jul. 17, 2009, now Pat. No. 8,075,136, application No. 13/620,486, which is a continuation-in-part of application No. 12/793,989, filed on Jun. 4, 2010, now Pat. No. 8,702,234, which is a continuation of application No. 12/505,193, filed on Jul. 17, 2009, now Pat. No. 8,075,136, which is a division of application No. 11/224,774, filed on Sep. 13, 2005, now Pat. No. 7,575,321, which is a continuation-in-part of application No. 10/697,454, filed on Oct. 30, 2003, now Pat. No. 7,708,403.

(60) Provisional application No. 61/700,782, filed on Sep. 13, 2012, provisional application No. 61/047,935, filed on Apr. 25, 2008.

(51) Int. Cl.
*A61B 5/145* (2006.01)
*A61B 3/02* (2006.01)

(56) References Cited

U.S. PATENT DOCUMENTS

| | | | |
|---|---|---|---|
| 4,445,516 A | 5/1984 | Wollnik et al. | |
| 4,889,422 A | 12/1989 | Pavlidis | |
| 5,065,767 A | 11/1991 | Maddess | |
| 5,295,495 A | 3/1994 | Maddess | |
| 5,474,081 A | 12/1995 | Livingstone et al. | |
| 5,539,482 A | 7/1996 | James et al. | |
| 5,595,883 A | 1/1997 | Appleyard et al. | |
| 5,704,369 A | 1/1998 | Scinto et al. | |
| 5,713,353 A | 2/1998 | Castano | |
| 5,778,893 A | 7/1998 | Potter | |
| 5,830,139 A | 11/1998 | Abreu | |
| 5,894,338 A | 4/1999 | Miehle et al. | |
| 5,912,723 A | 6/1999 | Maddess | |
| 6,024,450 A | 2/2000 | Ishikawa et al. | |
| 6,033,076 A * | 3/2000 | Braeuning et al. | 351/224 |
| 6,068,377 A | 5/2000 | McKinnon et al. | |
| 6,113,537 A | 9/2000 | Castano | |
| 6,120,460 A | 9/2000 | Abreu | |
| 6,123,668 A | 9/2000 | Abreu | |
| 6,123,943 A | 9/2000 | Baba et al. | |
| 6,129,682 A | 10/2000 | Borchert et al. | |
| 6,247,812 B1 | 6/2001 | Miehle et al. | |
| 6,305,804 B1 | 10/2001 | Rice et al. | |
| 6,312,393 B1 | 11/2001 | Abreu | |
| 6,315,414 B1 | 11/2001 | Maddess et al. | |
| 6,423,001 B1 | 7/2002 | Abreu | |
| 6,477,394 B2 | 11/2002 | Rice et al. | |
| 6,556,853 B1 | 4/2003 | Cabib et al. | |
| 6,603,552 B1 | 8/2003 | Cline et al. | |
| 7,050,087 B2 | 5/2006 | Harari et al. | |
| 7,166,079 B2 | 1/2007 | Febbroriello et al. | |
| 7,232,220 B2 | 6/2007 | Franz et al. | |
| 7,237,898 B1 | 7/2007 | Hohla et al. | |
| 7,575,321 B2 | 8/2009 | Newman et al. | |
| 7,708,403 B2 | 5/2010 | Newman | |
| 2002/0097379 A1 | 7/2002 | Goldfain et al. | |
| 2002/0106617 A1 | 8/2002 | Hersh | |
| 2004/0105073 A1 | 6/2004 | Maddalena et al. | |
| 2005/0243277 A1 | 11/2005 | Nashner | |
| 2006/0025658 A1 | 2/2006 | Newman et al. | |
| 2009/0270717 A1 | 10/2009 | Newman | |
| 2010/0014050 A1 | 1/2010 | Newman et al. | |
| 2010/0238405 A1 | 9/2010 | Newman et al. | |

FOREIGN PATENT DOCUMENTS

| | | |
|---|---|---|
| EP | 1127534 | 8/2001 |
| EP | 1219243 | 7/2002 |
| EP | 1527731 | 5/2005 |
| FR | 2593381 | 7/1987 |
| WO | WO98/57579 | 12/1998 |
| WO | WO02/41108 | 5/2002 |
| WO | WO2004/084117 | 9/2004 |
| WO | WO2007/061469 | 5/2007 |

OTHER PUBLICATIONS

Silva et al., Independent Patterns of Damage with Magno-, Parvo- and Koniocellular Pathways in Parkinson's Disease, Brain (Oct. 2005) 128 (10); 2260-2271.

Ruseckaite et al., "Frequency Doubling Illusion VEPs and Automated Perimetry in Multiple Sclerosis." Doc Ophtalmol. Jul. 2006; 113(10); 29-41, Epub Aug. 12, 2006.

Valenti et al., "To Discuss the Deficits in the Visual Pathway of Those with Parkinson's Disease (PD) as Measured by Frequency Doubling Technology (FDT), Optical Coherence Tomography (OCT) and Magnetic Resonance Imaging (MRI)." ARVO 2005 Abstracts http://www.arvo.org/EWEB/dynamicPage.aspx?WebCode=2005abstracts&site=isie.

Valenti. "Optometrist <Oderates ARVO Panel, Presents Pharmacology Lecture," American Optometric Association News, vol. 45, No. 16, May 14, 2007, p. 7.

S.Sokol; "The Visually Evoked Cortical Potential in the Optic Nerve and Visual Pathway Disorders;" published in "Electrophysiological Testing in Diseases of the Retina, Optic Nerve, and Visual Pathway;" edited by G.A. Fishman; published by the American Academy of Opthalmology, San Francisco in 1990, vol. 2, pp. 105-141.

Clark Tsai; "Optic Nerve Head and Nerve Fiber Layer in Alzheimer's Disease;" Published in Arch. of Opthalmology, vol. 107, Feb. 1991. Sarah Muscat, Stuart Parks, Ewan Kemp, and David Keating; "Repeatability in Reproducibility of Macular Thickness Measurements with the Humphrey OCT System;" Published in IVOS, Feb. 2002, vol. 43, No. 2 (6 pages).

European Search Report for 06801682.3, dated Jan. 14, 2010 (15 pages).

European Search Report for 04025213.2, dated Feb. 16, 2005 (5 pages).

International Search Report for PCT/US2006/032065, dated Apr. 3, 2007 (5 pages).

Extended European Search Report for 06801682.3, dated Oct. 9, 2009 (16 pages).

* cited by examiner

EYE CONTRAST SENSITIVITY ZONE MAP

Contrast Sensitivity Test Output File Parameters

| Parameter Name | Definition |
|---|---|
| "Age" | The age of the subject |
| "LeftDurationTime" | The test duration time of left eye |
| "RightDurationTime" | The test duration time of right eye |
| "MDLeftEye" | The mean deviation of left eye directly from FDT printout |
| "MDRightEye" | The mean deviation of right eye directly from FDT printout |
| "PSDLeftEye" | The pattern standard deviation of left eye directly from FDT printout |
| "PSDRightEye" | The pattern standard deviation of right eye directly from FDT printout |
| "PeripheryLeftEye" | Calculated as average of thresholds in periphery area on the left eye (#1, #2, #3, #4, #5, #6, #7, #8, #9, #10, #11, #12, #17, #18, #19, #20, #25, #26, #27, #29, #30, #35, #36, #37, #38, #39, #44, #45, #46, #47, #48, #49, #50, #51, #52, #53, #54, #55); (N = 38) |
| "PeripheryRightEye" | Calculated as average of thresholds in periphery area on the right eye (#1, #2, #3, #4, #5, #6, #7, #8, #9, #10, #11, #12, #17, #18, #19, #20, #21, #26, #27, #29, #30, #31, #36, #37, #38, #39, #44, #45, #46, #47, #48, #49, #50, #51, #52, #53, #54, #55); (N = 38) |
| "CentralLeftEye" | Calculated as average of thresholds in central area on the left eye (#13, #14, #15, #16, #21, #22, #23, #24, #31, #32, #33, #34, #40, #41, #42, #43, #28); (N = 17) |
| "CentralRightEye" | Calculated as average of thresholds in central area on the right eye (#13, #14, #15, #16, #22, #23, #24, #25, #32, #33, #34, #35, #40, #41, #42, #43, #28); (N = 17) |
| "SuperiorLeftEye" | Calculated as average of thresholds in the superior area on the left eye (#1, #2, #3, #4, #5, #6, #7, #8, #9, #10, #11, #12, #13, #14, #15, #16, #17, #18, #19, #20, #21, #22, #23, #24, #25, #26, #27); (N = 27) |
| "SuperiorRightEye" | Calculated as average of thresholds in the superior area on the right eye (#1, #2, #3, #4, #5, #6, #7, #8, #9, #10, #11, #12, #13, #14, #15, #16, #17, #18, #19, #20, #21, #22, #23, #24, #25, #26, #27); (N = 27) |
| "InferiorLeftEye" | Calculated as average of thresholds in the inferior area on the left eye (#29, #30, #31, #32, #33, #34, #35, #36, #37, #38, #39, #40, #41, #42, #43, #44, #45, #46, #47, #48, #49, #50, #51, #52, #53, #54, #55); (N = 27) |
| "InferiorRightEye" | Calculated as average of thresholds in the inferior area on the right eye (#29, #30, #31, #32, #33, #34, #35, #36, #37, #38, #39, #40, #41, #42, #43, #44, #45, #46, #47, #48, #49, #50, #51, #52, #53, #54, #55); (N = 27) |

FIG. 3B

| | |
|---|---|
| "Superior10LeftEye" | Calculated as average of thresholds in the superior 10 degree around 12:00 on the clock on the left eye (#2 #3 #7 #8 #14 #15 #22 #23); (N = 8) |
| "Superior10RightEye" | Calculated as average of thresholds in the superior 10 degree around 12:00 on the clock on the right eye (#2 #3 #7 #8 #14 #15 #23 #24); (N = 8) |
| "Inferior10LeftEye" | Calculated as average of thresholds in the inferior 10 degree around 6:00 on the clock on the left eye (#32 #33 #41 #42 #48 #49 #53 #54); (N = 8) |
| "Inferior10RightEye" | Calculated as average of thresholds in the inferior 10 degree around 6:00 on the clock on the left eye (#33 #34 #41 #42 #48 #49 #53 #54); (N = 8) |
| "SuperiorVerticalLeftEye" | Calculated as average of thresholds (#5 #12 #20, three zones superior to the optic disc in the left eye) |
| "SuperiorVerticalRightEye" | Calculated as average of thresholds (#10 #17 #26, three zones superior to the optic disc in the right eye) |
| "MacularArcLeftEye" | Calculated as average of thresholds (#20 #21 #22 #28, macular zone and the three superior zones between the macula and the optic disc) |
| "MacularArcRightEye" | Calculated as average of thresholds (#24 #25 #26 #28, macular zone and the three superior zones between the macula and the optic disc) |
| "SuperiorQuadLeftEye1" | Calculated as average of thresholds in the left superior quad on the left eye (#1 #2 #5 #6 #7 #11 #12 #13 #14 #19 #20 #21 #22); (N = 13) |
| "SuperiorQuadLeftEye2" | Calculated as average of thresholds in the right superior quad on the left eye (#3 #4 #8 #9 #10 #15 #16 #17 #18 #23 #24 #25 #26 #27); (N = 14) |
| "InferiorQuadLeftEye1" | Calculated as average of thresholds in the left inferior quad on the left eye (#29 #30 #31 #32 #38 #39 #40 #41 #46 #47 #48 #52 #53); (N = 13) |
| "InferiorQuadLeftEye2" | Calculated as average of thresholds in the right inferior quad on the left eye (#32 #34 #35 #36 #37 #42 #43 #44 #45 #49 #50 #51 #54 #55); (N = 14) |
| "SuperiorQuadRightEye1" | Calculated as average of thresholds in the left superior quad on the right eye (#1 #2 #5 #6 #7 #11 #12 #13 #14 #19 #20 #21 #22 #23); (N = 14) |
| "SuperiorQuadRightEye2" | Calculated as average of thresholds in the right superior quad on the right eye (#3 #4 #8 #9 #10 #15 #16 #17 #18 #24 #25 #26 #27); (N = 13) |
| "InferiorQuadRightEye1" | Calculated as average of thresholds in the left inferior quad on the right eye (#29 #30 #31 #32 #33 #38 #39 #40 #41 #46 #47 #48 #52 #53); (N = 14) |
| "InferiorQuadRightEye2" | Calculated as average of thresholds in the right inferior quad on the right eye (#34 #35 #36 #37 #42 #43 #44 #45 #49 #50 #51 #54 #55); (N = 13) |

| SUBJECT | PERSONAL ATTRIBUTES | CONTRAST SENSITIVITY TEST RESULTS | ACTUAL CLINICAL HEALTH CLASSIFICATION |
|---|---|---|---|
| 0538416 | NAME: AGE: GENDER: . . . | LEFT DURATION TIME: RIGHT DURATION TIME: MD LEFT EYE: . . . INFERIOR QUAD... | AD |
| 0612781 | NAME: AGE: GENDER: . . . | LEFT DURATION TIME: . . . INFERIOR QUAD... | NH |
| . . . | . . . | . . . | . . . |

FIG. 5B

FIG. 6A $P_1$ = Probability of appropriate classification as Normal Health.

$P_2$ = Probability of appropriate classification as Cognitive Complaint $P_3$ = Probability of appropriate classification as Mild Cognitive Impairment $P_4$ = Probability of being appropriate classification as Alzheimer's Disease $$P_1 = 1 - P_2 - P_3 - P_4 \qquad (0)$$

$$\log \frac{P_2}{P_1} = a_1 x + b_1; \qquad (1)$$

$$\log \frac{P_3}{P_1} = a_2 x + b_2; \qquad (2)$$

$$\log \frac{P_4}{P_1} = a_3 x + b_3; \qquad (3)$$

$$P_1 = \frac{1}{1 + \Sigma_i e^{a_i x + b_i}} \qquad (4)$$

$$P_2 = \frac{e^{a_1 x + b_1}}{1 + \Sigma_i e^{a_i x + b_i}} \qquad (5)$$

$$P_3 = \frac{e^{a_2 x + b_2}}{1 + \Sigma_i e^{a_i x + b_i}} \qquad (6)$$

$$P_4 = \frac{e^{a_3 x + b_3}}{1 + \Sigma_i e^{a_i x + b_i}} \qquad (7)$$

| SUBJECT | PERSONAL ATTRIBUTES | CONTRAST SENSITIVITY TEST RESULTS | PROBABILISTIC HEALTH CLASSIFICATION(S) |
|---|---|---|---|
| 0395012 | NAME:... AGE:... GENDER:... | LEFT DURATION TIME: ... INFERIOR QUAD... | AD:53% MCI:28% CC:15% NH:4% |
| 7843125 | NAME: AGE: GENDER: | LEFT DURATION TIME: ... INFERIOR QUAD... | AD:8% MCI:17% CC:14% NH:61% |
| | | | |

FIG.6B

| ACTUAL \ PREDICTED | NH | CC | MCI | AD | TOTAL ACTUAL |
|---|---|---|---|---|---|
| NH | 26 | | 3 | | 29 |
| CC | 11 | | 7 | | 18 |
| MCI | 8 | | 17 | 2 | 27 |
| AD | 1 | 0 | 7 | 1 | 9 |
| TOTAL PREDICTED | 46 | 0 | 34 | 3 | 83 |

Health Correlation Assessment Based Upon
Multiple Contrast Sensitivity Measurement Parameters

*RightDurationTime*, is the duration time of the test on the right eye.

$PeriCenRatioRightEye = \frac{|PeripheryRightEye - CentralRightEye|}{PeripheryRightEye + CentralRightEye}$, compares the periphery area and central area of the right eye.

$SupInfRatioRightEye = \frac{|SuperiorRightEye - InferiorRightEye|}{SuperiorRightEye + InferiorRightEye}$, compares the superior and inferior hemifields of the right eye.

*MacularArcRightEye* measures the four zones between the optic disc and the macula in the right eye.

$SuperiorQuadRatioRightEye = \frac{|SuperiorQuadRightEye1 - SuperiorQuadRightEye2|}{SuperiorQuadRightEye1 + SuperiorQuadRightEye2}$, compares the right and left superior quadrants of the right eye.

$$P_1 = 1 - P_2 - P_3 - P_4 \qquad (0)$$

$$log\frac{P_2}{P_1} = a_{11}x_1 + a_{12}x_2 + a_{13}x_3 + a_{14}x_4 + a_{15}x_5 + b_1; \qquad (11)$$

$$log\frac{P_3}{P_1} = a_{21}x_1 + a_{22}x_2 + a_{23}x_3 + a_{24}x_4 + a_{25}x_5 + b_2; \qquad (12)$$

$$log\frac{P_4}{P_1} = a_{31}x_1 + a_{32}x_2 + a_{33}x_3 + a_{34}x_4 + a_{35}x_5 + b_3; \qquad (13)$$

$$P_1 = \frac{1}{1 + \sum_i e^{a_{i1}x_1 + a_{i2}x_2 + a_{i3}x_3 + a_{i4}x_4 + a_{i5}x_5 + b_i}} \qquad (14)$$

$$P_2 = \frac{e^{a_{11}x_1 + a_{12}x_2 + a_{13}x_3 + a_{14}x_4 + a_{15}x_5 + b_1}}{1 + \sum_i e^{a_{i1}x_1 + a_{i2}x_2 + a_{i3}x_3 + a_{i4}x_4 + a_{i5}x_5 + b_i}} \qquad (15)$$

$$P_3 = \frac{e^{a_{21}x_1 + a_{22}x_2 + a_{23}x_3 + a_{24}x_4 + a_{25}x_5 + b_2}}{1 + \sum_i e^{a_{i1}x_1 + a_{i2}x_2 + a_{i3}x_3 + a_{i4}x_4 + a_{i5}x_5 + b_i}} \qquad (16)$$

$$P_4 = \frac{e^{a_{31}x_1 + a_{32}x_2 + a_{33}x_3 + a_{34}x_4 + a_{35}x_5 + b_3}}{1 + \sum_i e^{a_{i1}x_1 + a_{i2}x_2 + a_{i3}x_3 + a_{i4}x_4 + a_{i5}x_5 + b_i}} \qquad (17)$$

| ACTUAL \ PREDICTED | NH | CC | MCI | AD | TOTAL ACTUAL |
|---|---|---|---|---|---|
| NH | 24 | 2 | 3 | 0 | 29 |
| CC | 8 | 4 | 6 | 0 | 18 |
| MCI | 6 | 2 | 18 | 1 | 27 |
| AD | 0 | 1 | 4 | 4 | 9 |
| TOTAL PREDICTED | 38 | 9 | 31 | 5 | 83 |

FIG.11

APPARATUS FOR HEALTH CORRELATION ASSESSMENT

CROSS REFERENCE TO RELATED APPLICATIONS

This document is a U.S. non-provisional utility patent application that claims priority and benefit to, U.S. non-provisional patent application Ser. No. 12/794,053 and Ser. No. 12/793,989, which were both filed on Jun. 4, 2010, and are entitled "Diagnosis of Optically Identifiable Ophthalmic Conditions". Both of the aforementioned patent applications are continuation patent applications of, and claim priority and benefit to, U.S. non-provisional utility patent application Ser. No. 12/505,193 that was filed on Jul. 17, 2009, entitled "Apparatus and Method for Diagnosis of Optically Identifiable Ophthalmic Conditions" and that has issued as U.S. Pat. No. 8,075,136, and which is a continuation patent application of, and claims priority and benefit to, U.S. patent application Ser. No. 11/224,774 that was filed on Sep. 13, 2005, and that has issued U.S. Pat. No. 7,575,321, which is a continuation-in-part application of, and claims the priority and benefit to, U.S. patent application Ser. No. 10/697,454 that was filed Oct. 30, 2003, and that has issued as U.S. Pat. No. 7,708,403. Priority is claimed to all of the aforementioned patent applications, which are incorporated herein by reference in their entirety.

This document further claims priority and benefit to, U.S. non-provisional utility patent application Ser. No. 12/430,202 filed on Apr. 27, 2009, that is entitled "Apparatus and Method for Diagnosis of Optically Identifiable Ophthalmic Conditions", which claims priority and benefit to U.S. provisional utility patent application Ser. No. 61/047,935 that was filed on Apr. 25, 2008. Priority is claimed to all of the aforementioned patent applications, which are incorporated herein by reference in their entirety.

This document further claims priority and benefit to, U.S. provisional utility patent application Ser. No. 61/700,782 (Confirmation No. 7817) filed on Sep. 13, 2012, that is entitled "Apparatus for Health Correlation Assessment", and which is also incorporated herein by reference in its entirety.

JOINT RESEARCH AGREEMENT

The subject matter of this invention includes the processing of data obtained from a joint research agreement between the Assignee of the present application and Andrew Saykin of Indiana University, Center for Neuroimaging, Dept. of Radiology. Indiana University School of Medicine, 959 W. Walnut St. R2EH24, Indianapolis. Ind. and Laura Flashman, Dartmouth College, Dept. of Psychiatry, Dartmouth College Medical School, Lebanon, N.H.

BACKGROUND OF THE INVENTION

People residing within certain health classifications, such as those people afflicted with Alzheimer's disease, require a substantial amount of costly medical and non-medical care during the period of time in which they are afflicted with such a debilitating disease. The amount of required care typically escalates as the disease progresses. Also, as the disease progresses, it becomes more likely that the disease will facilitate, but not necessarily cause, pre-mature 1 death of the afflicted person.

Some health care professionals believe that early detection and treatment of Alzheimer's disease could eventually slow progression of the disease, reduce the amount and cost of long term care required to be provided to such a person, and in some circumstances, enable a person to delay and/or even avoid the most severe stages of the disease prior to the eventual death of that person. Technology that can provide early detection of Alzheimer's disease at a cost that is substantially less than the cost of existing methods of detection is needed. Such technology could reduce the massive projected costs of caring for future Alzheimer's patients.

The discussion above is merely provided for general background information and is not intended to be used as an aid in determining the scope of the claimed subject matter.

BRIEF DESCRIPTION OF THE INVENTION

The invention relates to an apparatus, system and method for performing a health correlation assessment based upon results an eye contrast sensitivity measurement test of a person. The health correlation assessment provides information conveying a relative probability (likelihood) of the person being appropriately assigned into a particular clinical health classification based upon some standard of clinical testing. In some embodiments, the health correlation assessment is quantitative and provides a set of one or more numerical probabilities as a predictive estimate of the likelihood of the person being appropriately assigned into a particular clinical health classification.

Such an eye contrast sensitivity measurement can be used to identify (predict) those people who are more likely to be appropriately classified within a pre-clinical Alzheimer's disease state (e.g. cognitive complaint and mild cognitive complaint) or within Alzheimer's disease state of health (e.g. mild, moderate, and severe), and who should seek further clinical testing to ascertain their actual clinical health status, and to determine a course of treatment, and to track a rate of progression of the disease.

This brief description of the invention is intended only to provide a brief overview of subject matter disclosed herein according to one or more illustrative embodiments, and does not serve as a guide to interpreting the claims or to define or limit the scope of the invention, which is defined only by the appended claims.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention can encompass other equally effective embodiments. The drawings are not necessarily to scale. The emphasis of the drawings is generally being placed upon illustrating the features of certain embodiments of the invention. In the drawings, like numerals are used to indicate like parts throughout the various views. Differences between like parts may cause those parts to be indicated with different numerals. Unlike parts are indicated with different numerals. Thus, for further understanding of the invention, reference can be made to the following detailed description, read in connection with the drawings in which:

FIG. 2 illustrates a map of retinal zones employed within an eye contrast sensitivity test measurement (FDT) device.

FIGS. 3A-3B list an embodiment of a set of contrast sensitivity test (CST) output file parameters of the FDT device of FIG. 1.

FIGS. 5A-5B illustrate a health correlation assessment procedure algorithm (HCAPPA) coefficient generation process in which multiple types of data are processed.

FIGS. 6A-6B illustrate a single CST parameter correlation model associated with a first embodiment a health correlation assessment program predictive algorithm (HCAPPA).

FIG. 9 is a matrix illustrating a relationship between the results of the predicted and actual clinical health classifications based upon the single CST parameter correlation model of FIG. 6A.

FIG. 10 illustrates a multiple CST parameter correlation model associated with a second embodiment of the correlation assessment procedure predictive algorithm (HCAPPA).

FIG. 11 is a matrix illustrating a relationship between the results of the predicted and actual clinical health classifications based upon the multiple CST parameter correlation model of FIG. 10.

DETAILED DESCRIPTION OF THE INVENTION

Figure 1:
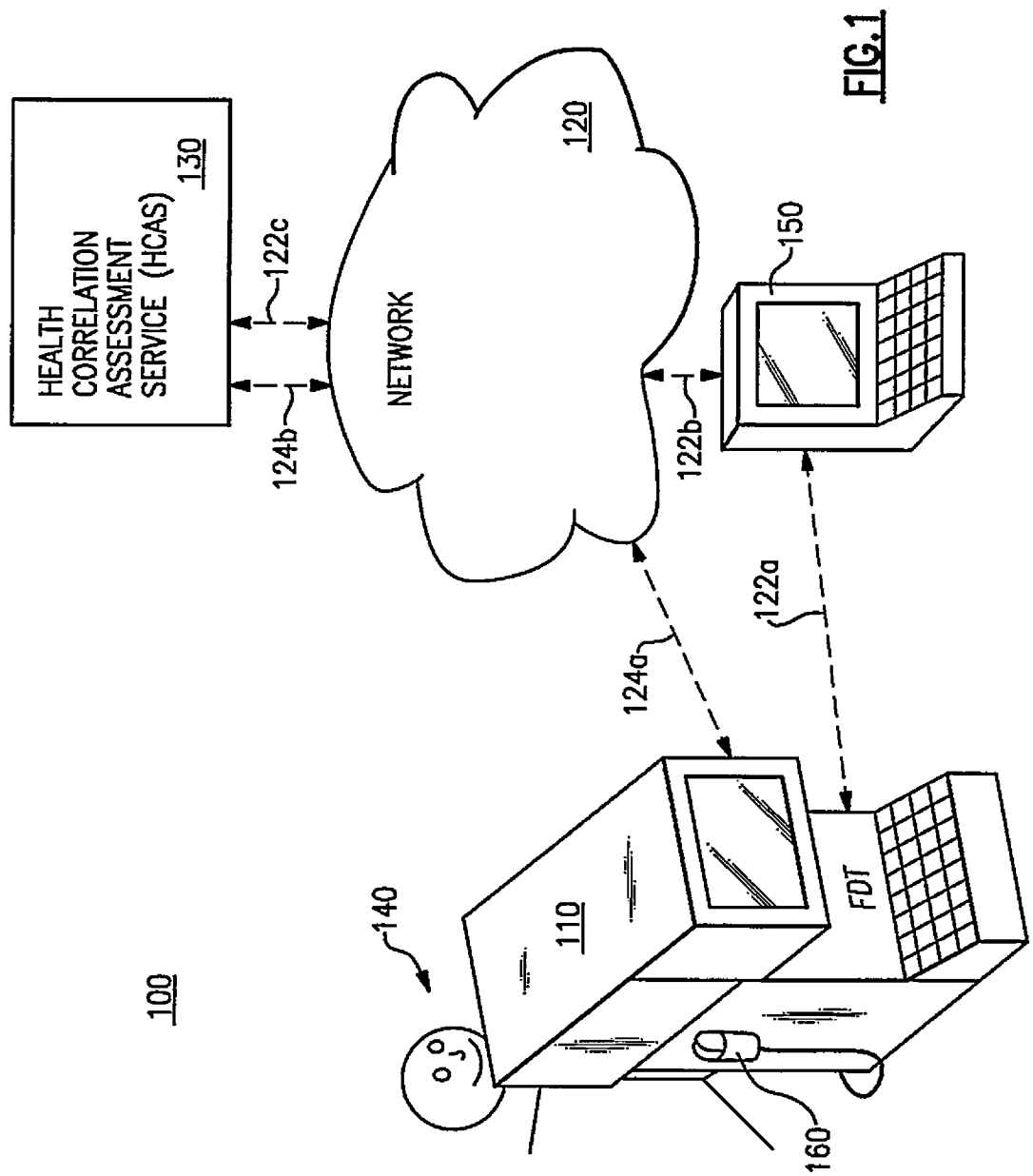
FIG. 1 illustrates communication between an eye contrast sensitivity test (CST) measurement device and a health correlation assessment service.

FIG. 1 illustrates communication between an eye contrast sensitivity test (CST) measurement device 110 and a health correlation assessment service (HCAS) 130. The HCAS 130 incorporates computing resources having access to algorithmic procedures based upon clinical and CST data that support performance of health correlation assessment. The eye contrast sensitivity measurement device 110, also referred to as a frequency doubling technology (FDT) device 110, is designed to project images onto the eyes of a subject, also referred to herein as the viewer 140. The images are projected during intermittent time intervals and at various locations within the field of view of the viewer, and contain contrast patterns that are dynamically altered over time. See U.S. Pat. No. 8,073,136 which is incorporated herein by reference. The viewer 140 provides a response to the FDT device 110 upon detecting the presence of a contrast image during a period of time.

The results of each contrast sensitivity test (CST) eye examination are stored into an output file within non-volatile memory storage, such as a disk storage device, residing within the FDT device 110. The content of the file can be stored into various file formats, including such as .FDT, .PDF or .XML file formats.

In accordance with the invention, the output file can be further communicated (copied) to a location that is outside of the FDT device 110. Such communication can be performed via a communication path 124a to a network 120, such as the internet, and/or via a communication path 124b to web accessible sites located on the internet including a health correlation assessment service (HCAS) site 130. The FDT device 110 can also have a communication path 122a to another computer 150 via a direct connection or via a network, including such as the internet. The computer 150 can act as an intermediary for access to the HCAS 130 via communication links 122b-122c to the internet. The FDT device 110 can also communicate the output file via a portable memory device (media), such as via a compact disc or a universal serial bus (USB) compatible memory device to another computer 150.

Figure 2:
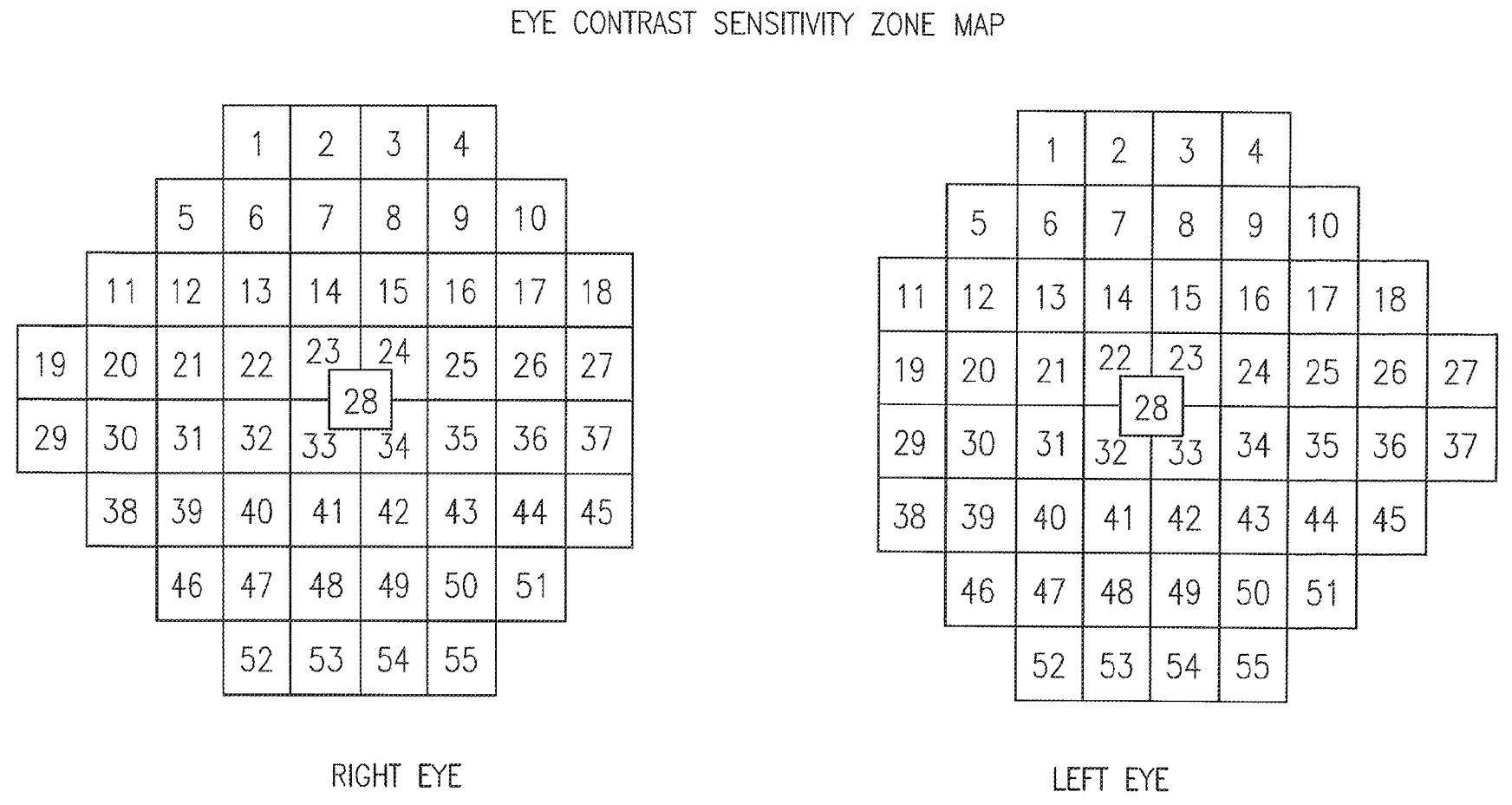

Alternately, in some embodiments, the HCAS 130 and the computer 150 can be incorporated within the FDT device 110, having access to the output file that is stored local to the FDT device 110. In other embodiments, the HCAS 130 executes on the computer 150 which has access to a copy of the output file FIG. 2 illustrates a map of retinal zones employed within an eye contrast sensitivity measurement (FDT) device 110. As shown, in this embodiment, there are (55) zones that occupy the field of view of each eye of the viewer and that are arranged and numbered from a viewing perspective of the FDT device 110 towards the subject (viewer) being tested. Note that other embodiments of contrast sensitivity measurement may employ different arrangements to map the field of view of the viewer.

During a contrast sensitivity examination (test), the FDT device 110 projects contrast patterns at locations within the selected (55) zones of the viewer's field of view. The viewer responds by pressing a button (160) in communication with the FDT device 110 when a contrast pattern is recognized.

Upon completion of a contrast sensitivity test, the FDT device 110 outputs test results into an output file. The output file includes a set of information quantifying the test performance of the viewer. The test results include a plurality of individual parameters. Some of these parameters measure test performance in association with a particular zone, while other parameters measure performance in association with a set of more than one zone, or in association with the contrast sensitivity test as a whole. In some embodiments, the output file may also include other information, including personal attributes including such as the name, gender and date of birth of the viewer.

FIGS. 3A-3B list an embodiment of a set of contrast sensitivity test (CST) output file parameters of the FDT device of FIG. 1. Of the (31) listed CST output file parameters, the last (24) CST parameters are explicitly defined to directly incorporate contrast sensitivity threshold values as measured for specific retinal zones. For example, the value of the "Superior10LeftEye" CST parameter is defined as an average of measured contrast sensitivity thresholds for (8) retinal zones 2-3, 7-8, 14-15 and 22-23.

Conversely, the first listed parameter "Age", is a personal attribute that is provided by the subject as part of performance of the contrast sensitivity test procedure and is not itself, a contrast sensitivity measurement. The "LeftDurationTime" and "RightDurationTime" values measure time required to complete the contrast sensitivity test for each of the left and right eyes. The "MDLeftEye" and "MDRightEye" are mathematical representations (mean deviation) for contrast sensitivity measurements of each of the left and right eyes. The "PSDLeftEye" and "PSDRightEye" are mathematical representations (pattern standard deviation) for contrast sensitivity measurements of each of the left and right eyes.

Embodiments of health correlation assessment procedures (HCAP) are designed to input and process some or all of the (31) listed CST output file parameter values and to output a health correlation assessment of the subject for which the CST parameters were measured. Other CST parameters can be created and defined based upon information obtained from the results of the contrast sensitivity test (See FIG. 10).

Figure 4A:
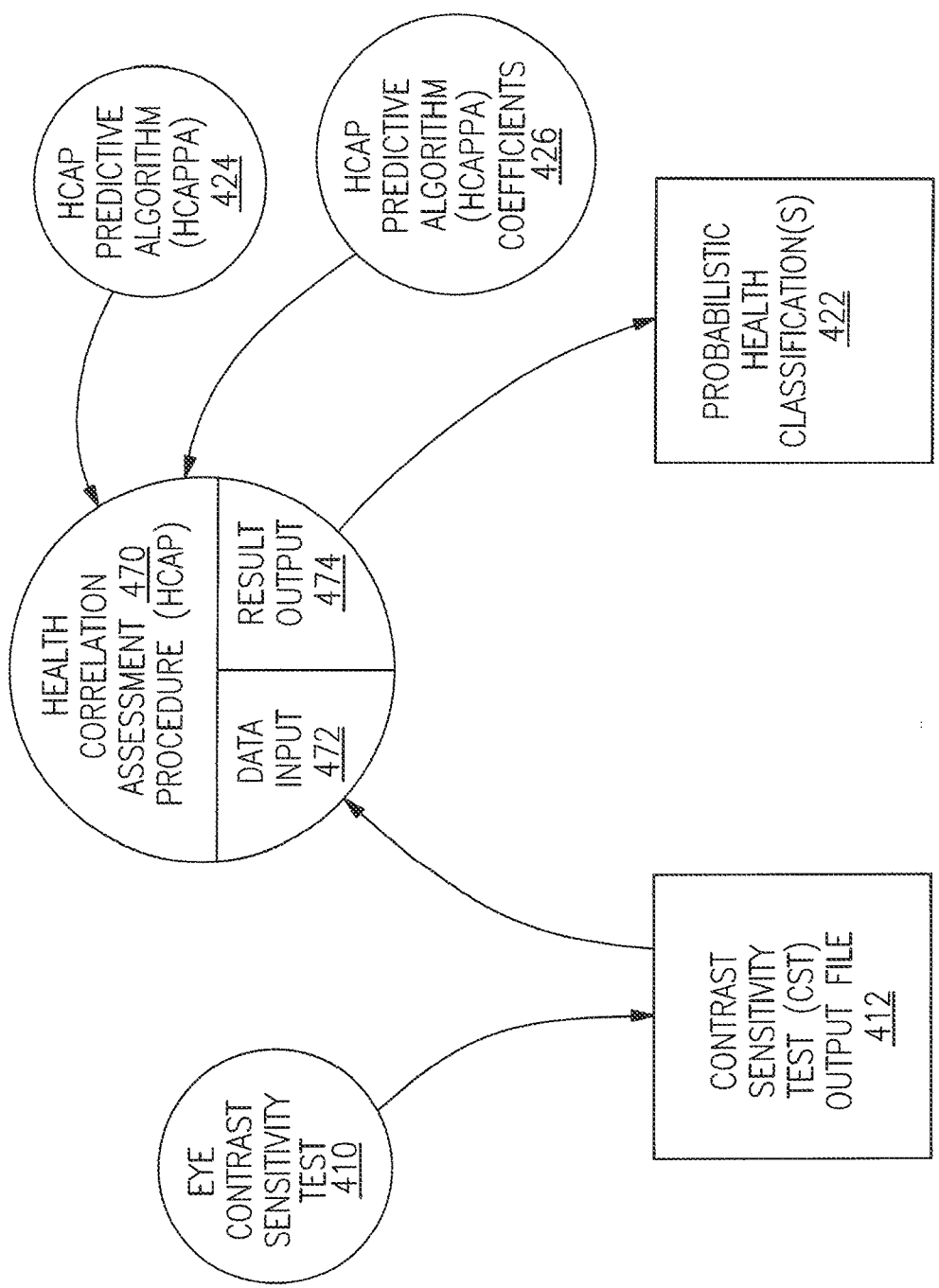
FIGS. 4A-4B illustrate the processing of contrast sensitivity measurement test (CST) result data by the health correlation assessment procedure (HCAP) implemented as computer software.
Figure 4B:
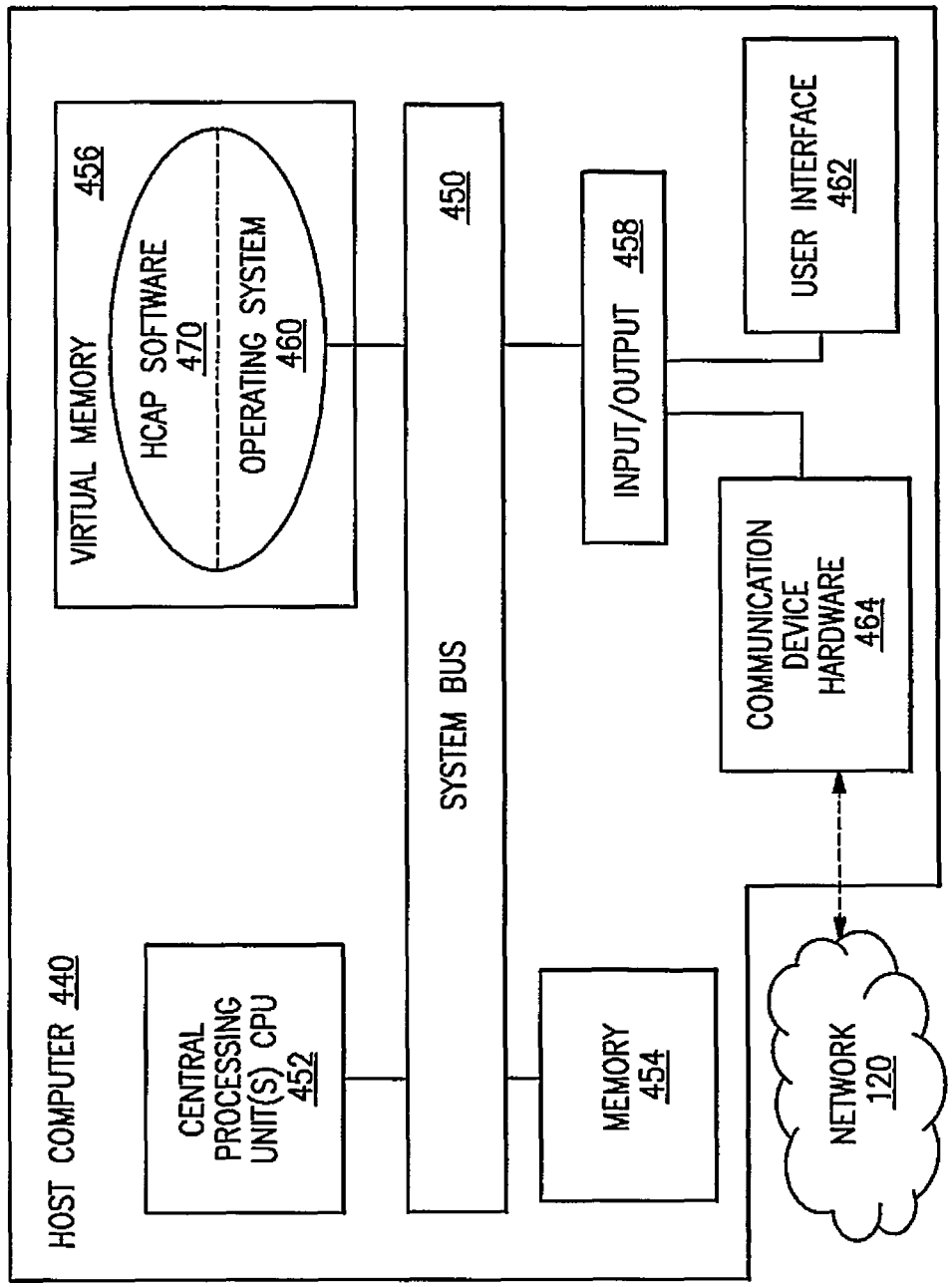

FIGS. 4A-4B illustrate the processing of contrast sensitivity measurement test result data by the health correlation assessment procedure (HCAP) implemented as computer software. FIG. 4A illustrates the processing of contrast sensitivity measurement test result data by the health correlation assessment procedure (HCAP) implemented as computer software 470.

As shown, results of a contrast sensitivity test 410 are stored as data for a subject into a contrast sensitivity test (CST) result output file 412. A health correlation assessment procedure (HCAP) 470 exercises a health correlation assessment procedure predictive algorithm (HCAPPA) which incorporates coefficient values. The HCAP 470 inputs and processes the content of the output file 412 via a data input component 472, and outputs one or more probabilistic health classification(s) 422 via a data output component. The HCAPPA determines a correlation based upon a correlation model, between the information content of the CST result output file 412 and one or more probabilistic health classification(s) 422.

The HCAPPA coefficient values 424 (a1, b1, a2, b2, a3 and b3) are incorporated into mathematical expressions (See equations (1)-(7) of FIG. 6A). The equations and coefficient values incorporated into those equations quantify a correlation between a set of one or more particular CST parameter values and a probabilistic health classification(s) 422, being a predictive probability of appropriate assignment of each subject receiving the one or more particular CST parameter values from results of a CST, to one or more particular clinical health classifications.

In a first embodiment of FIG. 6A, these coefficients are employed to compute a probabilistic health classification based upon a single contrast sensitivity test (CST) measurement parameter. In the embodiment of FIG. 10, other coefficients are employed to compute a probabilistic health classification based upon multiple contrast sensitivity test (CST) measurement parameters. These HCAPPA coefficients and their values are numerical values and are not the same and should not be confused with contrast sensitivity test (CST) parameters, which are each measurements of eye contrast sensitivity.

In some embodiments, the probabilistic health classification(s) 422 include at least one numerical probability of the subject's being appropriately classified into one or more health classifications based upon a correlation model. See equations (0) through (7) of FIG. 6A as an one example of an embodiment of a correlation model that is expressed via mathematical equations. This mathematical correlation model correlates at least a portion of the contrast sensitivity test result data for a subject with a probability of that subject being appropriately assigned into one or more clinical health classifications, in accordance with clinical criteria. In some embodiments, this mathematical correlation model is based upon a repository of information including results of a clinical evaluation for each of the subjects and including contrast sensitivity test result data for those subjects.

In some embodiments, the data input 472 component opens and processes (parses) the information content of the CST output file 412 in accordance with various file formats, including such as .FDT, .PDF or .XML file formats. The content of the CST output file 412 is parsed to identify each CST parameter value and personal attribute value residing therein, for input into the HCAP predictive algorithm (HCAPPA). For example, a CST output file 412 from the Zeiss manufactured FDT device provides CST related measurement information for the test taking subject, for each eye of the subject and for each retinal zone of each eye of the subject. This output file 412 basis, includes a measured contrast sensitivity threshold value, a total deviation value and a pattern deviation value expressed in decibels (dB), for each of the (55) retinal zones (See FIG. 2) of each eye of the test taking subject, as measured from within a contrast sensitivity test (CST). This output file 412 can further include some personal attribute information of the test taking subject, such as test subject name, age, and gender.

In some embodiments, the data input component 472 receives CST parameter values and/or other personal attribute values from other sources, such as via another data file, or via a communications channel with other CST related software and/or via a user interface with a user of the apparatus. For example, the HCAP data input component 472 may input subject age data from within the output file 412, but further input ethnicity or family history data associated with a subject from sources outside of the CST output file 412, such as via prompting and data entry of a user of the computer 150 or the FDT device 110.

In some embodiments, the data output component 474 outputs and represents probabilistic health classification(s) 422 quantitatively. For example, theses probabilistic health classification(s) can be expressed as "Alzheimer's Disease: 55%, "Normal Health: 45%". In some embodiments, probabilistic health classification(s) 422 are output and expressed qualitatively. For example, theses probabilistic health classification(s) can be expressed as "Alzheimer's Disease appears More Probable than Normal Health", and/or "Further clinical testing for Alzheimer's Disease is advised".

Note that in some circumstances, non-Alzheimer's disease related health information may be accessible to the HCAP 470 and output via the data output component 474 in combination with probabilistic health classification(s) 422. For example, the Zeiss FDT device 110 output file 412 provides information regarding a Glaucoma Hemi-field Test (GHT). The GHT is an indicator of a presence of Glaucoma. The Zeiss FDT output file 412 indicates whether GHT is "Within normal limits" or is not within normal limits. Such GHT related information indicates a relative (qualitative) probability of the test subject having Glaucoma in at least one eye. This GHT is a health classification assessment that is separate from any Alzheimer's Disease related probabilistic classification that may be provided by the HCAP 470.

Note that further clinical testing for glaucoma (e.g. visual field exam, intra-ocular pressure, and cup/disc ratio) is typically much less expensive that for Alzheimer's Disease (e.g. a battery of cognitive tests, MRI, and/or PET scan). In circumstances, where health classification assessment predicts a relative probability of the presence of both Glaucoma and Alzheimer's disease, it may be more cost effective to perform clinical tests for Glaucoma prior to possible tests for Alzheimer's Disease.

Like for Glaucoma, in some embodiments, the HCAP 470 will further provide information relating to a relative probability of the test subject being appropriately assigned to one or more than one non-Alzheimer's disease related health classifications including for example, at least one of glaucoma, Parkinson's disease, Multiple Sclerosis, and head trauma.

FIG. 4B illustrates a simplified representation of a host computer 440 that executes health correlation assessment program (HCAP) software. In some embodiments, the HCAP is implemented as a computer software program executing on a host computer 440. In some embodiments, the host computer 410 is a network accessible computer that provides computing support as part of the health correlation assessment service 130. In other embodiments, the host computer is a personal computer 150 separate from the FDT device 110. In other embodiments, the host computer 440 is a computer that is embedded within the FDT device 110.

In some embodiments (HCAP) software is stored as a computer program onto portable media, such as a compact disc or universal serial bus (USB) memory storage device. In some embodiments, the HCAP software interoperates with an operating system, such as for example, Microsoft Windows or LINIX operating systems, to access contrast sensitivity test and other personal attribute data of subjects to be health correlation assessed, to interact with a health correlation assessment service (HCAS) via network communication to access versions of parameters and/or algorithms for the assessment, and to interact with a user via a user interface.

In one embodiment, the HCAP software 470 is configured to inter-operate with an operating system 460, such as for example, a Microsoft Version 7 operating system via its application programming interface. The HCAP software 470 directs operations of a central processing unit (CPU) 452 that is accessible via a system bus 450 residing within the architecture of the host computer 440. User interface 462 hardware is available for the HCAP software 470 to direct interaction with a user and/or administrator of the host computer.

Alternatively, the HCAP software 470 is programmed to interoperate with other operating systems and/or computing platforms, such as for example, to interoperate with variants of UNIX, such as Linux or onto other Microsoft supplied operating systems, various IBM, real-time, or other operating systems. Preferably, the operating system 460 is designed to manage physical memory 454 as virtual memory 456 within which the HCAP software 470 resides.

Optionally, the host computer 440 operates and interfaces with a computer network 120 via input/output 458 and communication device hardware 464. The network can be implemented as a local or wide area network, to enable access to contrast sensitivity result output files from a variety of locations that are remote to the host computer 440.

In some embodiments, the HCAP 470 operates as part of a health correlation assessment service (HCAS) 130, which is implemented as a network accessible web site 130 via a private or public computer network, such as the Internet. In some embodiments, the method, apparatus or system of the invention, spans across state or national boundaries and may interoperate with a network that spans across state or national boundaries. For example, the host computer 440 can be located in the Canada while contrast sensitivity result output file data is accessed from locations within the United States and/or Canada. The HCAP software can be stored onto portable media, such as for example, a compact disc or a universal serial bus compatible memory device. In some embodiments, the host computer 440 is located within the FDT contrast sensitivity device 110 or within computer 150.

Figure 5A:
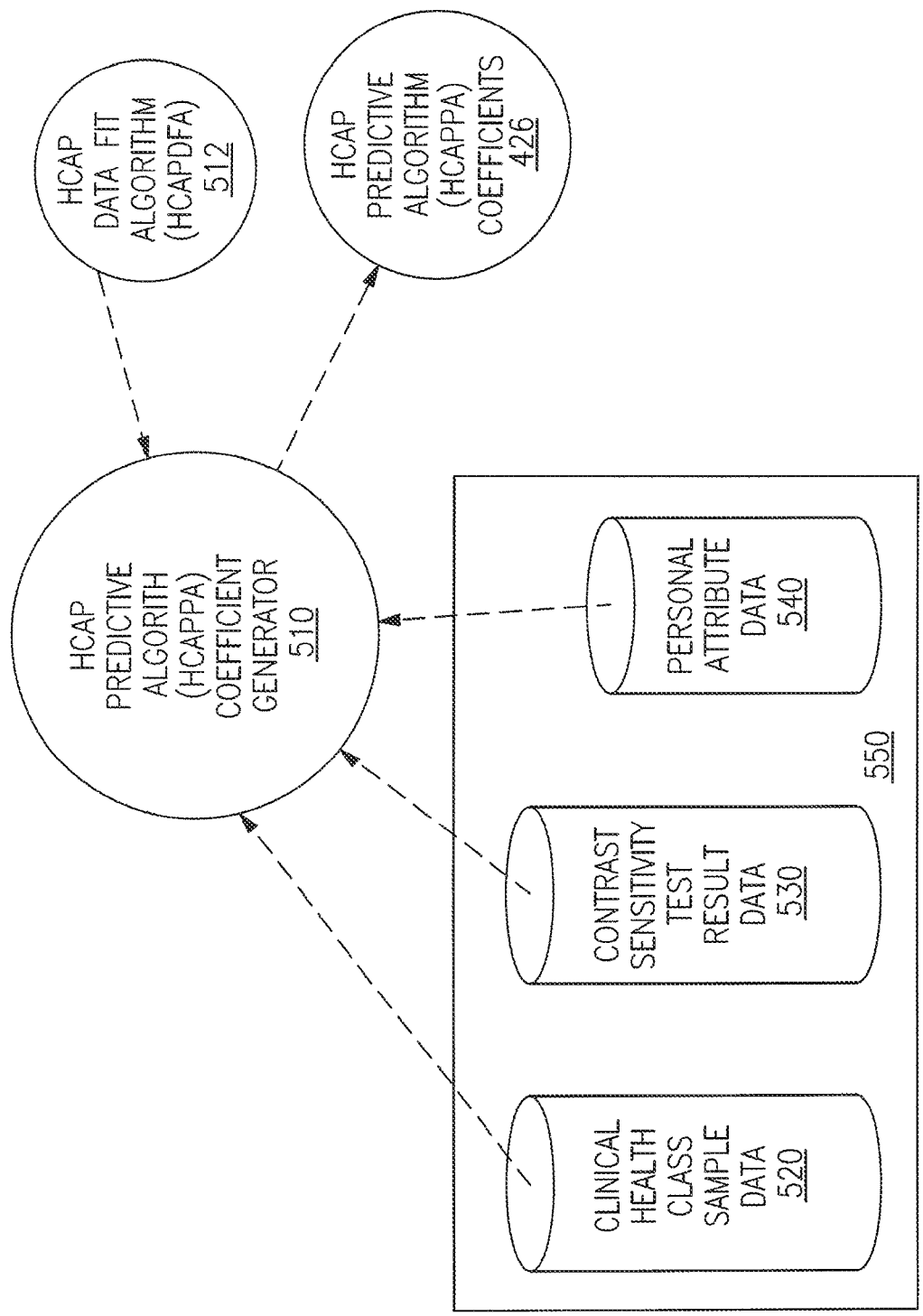

FIGS. 5A-5B illustrate a health correlation assessment procedure predictive algorithm (HCAPPA) coefficient generation process in which multiple types of sample data are processed. In one embodiment, this process is implemented as computer software, like the HCAP 470 of FIG. 4B. The HCAPPA coefficient generator software 510 processes a repository of sample data in order to generate coefficients for a particular embodiment of an HCAPPA algorithm.

In one embodiment, this coefficient generator 510 processes the sample data in accordance with the correlation model of FIG. 6A, and with equations (0) through (3) of FIG. 6A, and outputs HCAP algorithm coefficients 426 (a1, b1, a2, b2, a3 and b3) for incorporation into equations (4) through (7) of FIG. 6A. The equations and the variables and coefficients incorporated into these equations quantify a statistical correlation between a selected CST parameter value (See FIGS. 3A-3B) and a probability of appropriate assignment of each subject receiving the CST parameter value, to a particular clinical Alzheimer's related disease health classification.

Note that as referred to herein, a Alzheimer's related disease health classification includes pre-clinical stages of Alzheimer's disease, such as cognitive complaint(s) (CC), and clinical stages of the disease, such as mild cognitive impairment (MCI). The Alzheimer's Disease classification itself includes mild, moderate, and severe sub-classifications of the Alzheimer's Disease in accordance with applicable standards associated with the National Institute on Aging.

The health correlation assessment procedure predictive algorithm (HCAPPA) coefficient generator 510 inputs clinical health classification sample data 520, contrast sensitivity test result sample data 530 and optionally inputs personal attribute sample data 540 associated with each of a plurality of CST performing subjects from the sample data repository 550. The coefficients are determined so that the equations (0) through (4) incorporating these coefficients define a mathematical probability function that best fits with the sample data 530, 540 as plotted. Within these equations (0) through (4) of FIG. 6A, the variable (x) represents contrast sensitivity test (CST) values of one CST parameter. In other embodiments, an alternate correlation model inputs one or more values of a personal attribute, and/or inputs other CST parameter values that can be incorporated and designed into variations of equations like that of FIG. 6A FIG. 5B illustrates a representation of the types of sample data processed by HCAP predictive algorithm (HCAPPA) coefficient generator 510. Each subject is identified by a unique identifier 532, has associated personal attributes 534, associated contrast sensitivity test results 536 and an associated actual clinical health classification 538. These types of sample data for a plurality of subjects is stored within a repository. From these sources of sample data, health correlation assessment procedure algorithm (HCAPPA) coefficients 426 are determined and generated in accordance with equations (0) through (4) of FIG. 6A via the HCAP Data Fit algorithm HCAPDFA 512.

Referring back to FIGS. 1-5B, the HCAP 370 executes within the virtual memory address space 454 of the host computer 410 where ever the host computer 410 may reside. The HCAP 470 inputs and processes information from a contrast sensitivity test result output file 412, and outputs a probabilistic health classification 422 for the subject (viewer) 140 of the contrast sensitivity test. The probabilistic health classification is stored into a file 422 which can be displayed onto a user interface 462 of the host computer 440 and/or displayed onto a user interface of another computer, such as computer 150 for example, via communication of the probabilistic health classification to the another computer. In some embodiments, the another computer can be embedded or directly connected to the FDT device itself 110.

The HCAP executes an embodiment of a health correlation assessment procedure predictive algorithm (HCAPPA). In some embodiments, the HCAPPA is selectable from a plurality of different HCAPPA algorithms, via a command directive from within a configuration file or via a user interface by a user.

The scope of the invention described herein is not intended to be limited to any one algorithm or set of algorithms and/or to any set of procedures, variables and coefficients that are incorporated into an algorithm. Nor is the invention intended to be limited to each variable being defined to equal any particular CST parameter or combination of one or more CST parameters and/or personal attributes.

What is intended to be within the scope of the invention is that the health correlation assessment procedure (HCAP) processes at least one CST parameter value, of any type or of any combination of types, to provide a set of one or more probabilistic health classifications in response to the processed at least one CST parameter value. Optionally, the at least one CST parameter can be combined with other non-CST information (represented as non-CST parameters), such as for example, one or more attributes (age, gender, ethnicity, family history, work history, genetic or other types of biomarkers), of any type or of any combination of types, associated with the CST test taking subject, to provide the one or more probabilistic health classifications providing at least a minimum desired utility and accuracy of prediction.

The probabilistic health classifications provide a relative probability (prospect) of the first subject being appropriately assigned into at least one Alzheimer's disease related clinical health classification or at least one pre-clinical Alzheimer's disease classification. The relative probability can be expressed in a quantitative or qualitative manner to users of the health correlation assessment procedure (HCAP) and of the health correlation assessment system (HCAS). The relative probability or prospect provided by the probabilistic health classification is designed to provide information that reduces uncertainty regarding an appropriate clinical health classification to which the CST taking subject should be assigned. This probabilistic health classification information is provided in a manner that is separate from other information that could be acquired by clinical testing, but where such other information at a typically acquired at a much higher cost to the CST test taking subject.

In other embodiments, other algorithms can be designed to process a variety of one or more CST parameters in various combinations, and optionally in combination with one or more non-CST parameters such as personal attributes. Each CST parameter and personal attribute can be represented by one variable (x1, x2, . . . ) within an algorithm, or CST parameters and/or personal attribute values can be combined mathematically to define one variable (x1, x2, . . . ) within the algorithm. As the amount of Alzheimer's Disease related clinical data grows, it would be expected that specific algorithms would evolve to better exploit or attempt to exploit, a repository of Alzheimer's Disease related data of increasing size. It is foreseeable that many different types of algorithms can be employed with varying accuracy and effectiveness.

In one embodiment, the HCAPPA 424 selects and inputs one or more contrast sensitivity test (CST) parameters, also referred to herein as CST measurements, and outputs and a set of probabilistic health classifications for the subject performing the contrast sensitivity test. For example, the HCAPPA inputs a RightDurationTime CST parameter (See FIG. 3A) and outputs a set of probabilistic health classifications for the subject performing the contrast sensitivity test, based upon a quantified correlation between a contrast sensitivity test result value for the RightDurationTime parameter and clinical health classifications of sample subjects who also have known associated RightDurationTime CST parameter measurement values.

The RightDurationTime is defined as the time required for the subject to complete an entire contrast sensitivity test of the right eye. The amount of time required to complete an entire contrast sensitivity test is variable for each test subject and each eye. The right eye is typically the first eye to be tested, while the left eye is typically the second and last eye of the subject to be tested within the contrast sensitivity test.

Aside from the selection of a CST parameter, the design of the HCAPPA can vary with respect to a set of one or more probabilistic health classification(s) for which to predict. In one embodiment, the probabilistic health classification(s) include a first classification of Normal Health, and a second classification of Cognitive Complaint, third classification of Mild Cognitive Impairment and a fourth classification of Alzheimer's Disease.

In one embodiment, the HCAPPA outputs a probability of the subject's being appropriately classified into each of these (4) health classifications, based upon the value of the Right-DurationTime contrast sensitivity (CS) measurement parameter. In other embodiments, the HCAA outputs a probabilistic health classification based upon another set of one or more contrast sensitivity test (CST) measurements.

As an example, in one embodiment, the subject may receive a probabilistic health classification including the following set of probabilities: 10% of being Normal Health, 20% of being Cognitive Complaint, 40% of being Mild Cognitive Impairment, and 30% of being Alzheimer's disease. Alternatively, in another embodiment, the same probabilistic health classification can be represented by the above listed probabilities as 10% of being Normal Health and 90% of being of Non-Normal Health.

Appropriate assignment of a subject into a clinical health classification, depends upon other information (indicia) associated with the subject that is obtained from sources other than from an eye contrast sensitivity examination. This other information is obtained from clinical testing. Clinical testing involves performance of various clinical measurements and tests, including, for example, a beta-amyloid plaque deposit measurement, neurofibrillary tangle measurement, a cortex thickness measurement, volume and density of the hippocampus, and/or one or more cognitive tests performed upon the subject.

These clinical measurements and tests are performed in accordance with applicable standards and the results of which are interpreted by Alzheimer's disease and/or related disease specialists to decide appropriate placement of a subject into a particular clinical health classification. Such appropriate placement is referred to herein as an actual health classification, as opposed to a predicted health classification which results from exercise of the health correlation assessment algorithm (HCAA) alone.

The beta-amyloid plaque deposit and neurofibrillary tangle measurement can be determined via employment of a positron emission tomography (PET) scan using Pittsburgh Compound B (PiB) as a fluorescent trace substance. The cortex thickness measurement and volume and density of the hippocampus can be performed via an MRI scan. Cognitive tests can include the Mini-Mental State Examination (MMSE) and what is known as an MMSC cognitive test.

A combination of the above sources of other information is interpreted by the specialist(s) to determine whether a subject is appropriately classified into one of a set of defined health classifications. For example, a first set of health classifications includes Normal Health, Cognitive Complaint, Mild Cognitive Impairment and Alzheimer's disease health classifications.

In yet another embodiment, the probabilistic health classifications include only normal health and non-normal health. In this embodiment, subjects that would otherwise be classified as Cognitive Complaint or Mild Cognitive Impairment or as having Alzheimer's Disease would instead be classified as being of Non-Normal Health.

As referred to herein, Normal Health indicates the absence of clinical evidence for Alzheimer's disease and Mild Cognitive Impairment and Cognitive Complaint(s). However, a subject referred to herein as being appropriately classified as having Normal Health may be possibly afflicted with other non-Alzheimer's disease related ailments, such as Hepatitis C or a broken bone, for example. However, there is no known strong correlation between a contrast sensitivity examination and Hepatitis C or a broken bone within the subject and such non-Alzheimer's disease related ailments are ignored within the particular disclosed embodiments of the correlation model.

In another embodiment of the HCAPPA, the set of probabilistic health classifications exclude Cognitive Complaint and include Normal Health, Mild Cognitive Impairment and Alzheimer's disease. In this embodiment, subjects that would otherwise be classified as Cognitive Complaint would be instead classified as being of Normal Health. Mild Cognitive Impairment or Alzheimer's Disease.

FIG. 6A illustrates a first embodiment of a correlation model upon which a first embodiment of a health correlation assessment procedure predictive algorithm (HCAPPA) is based upon. As shown, $P_1$, also referred to herein as P1, represents a probability of a subject's being clinically classified as actually having Normal Health. $P_2$, also referred to herein as P2, represents a probability of a subject being clinically classified as actually having Cognitive Complaint(s) (CC). $P_3$, also referred to herein as P3, represents a probability of a subject's being clinically classified as actually having Mild Cognitive Impairment (MCI). $P_4$, also referred to herein as P4, represents a probability of a subject's being clinically classified as actually having Alzheimer's Disease. The Alzheimer's Disease classification includes mild, moderate, and severe sub-classifications of the Alzheimer's Disease in accordance with applicable standards associated with the Alzheimer's Disease Association.

In accordance with this correlation model, the above (4) probabilities (P1, P2, P3 and P4) are each a function of a selected CST parameter value, represented by the variable (x). Equation (0) indicates that P1+P2+P3+P4=1, meaning that for given value of (x), the (4) probabilities sum to the value 1 and there is no overlap between the probabilities associated with each of the (4) health classifications. Each probability represents a predictive likelihood that a subject (viewer) 140 receiving a CST parameter value (x), would be appropriately assigned to a particular health classification based upon clinical test and measurements performed separately from the contrast sensitivity test (CST).

In accordance with this correlation model, a subject (viewer) 140 can only be appropriately assigned to one health classification of the set consisting of Normal Health, Cognitive Complaint, Mild Cognitive Impairment and Alzheimer's Disease. A health care practitioner may advise that the subject should seek clinical testing to verify that the subject should or should not be assigned to the classification in which the subject receives the highest predictive probability from the HCAP. However the subject may also have other smaller and predictive probabilities of being appropriately assigned to one or more other health classifications within this probabilistic set, for which clinical testing may also be advisable.

Equation (1) indicates that the logarithm of the ratio of P2(x) divided by P1(x), which is equivalent to the logarithm of P2(x) minus the logarithm of P1(x), is expressed as a linear function. This linear function is defined as $(a_1x+b_1)$. Notice that within this correlation model, P1(x) and P2(x) are not limited to being linear functions and are free to be non-linear functions to better fit contrast sensitivity data. However, this model does require that the difference in the logarithm of P1(x) and logarithm of P2(x) be expressed as a linear function.

Equation (2) indicates that the logarithm of the ratio of P3(x) divided by P1(x), which is equivalent to the logarithm of P3(x) minus the logarithm of P1(x), is expressed as a linear function. This linear function is defined as $(a_2x+b_2)$. Notice that within this correlation model, P1(x) and P3(x) are not limited to being linear functions and are free to be non-linear functions to better fit contrast sensitivity data. However, this model does require that the difference in the logarithm of P1(x) and logarithm of P3(x) be expressed as a linear function.

Equation (3) indicates that the logarithm of the ratio of P4(x) divided by P1(x), which is equivalent to the logarithm of P4(x) minus the logarithm of P1(x), is expressed as a linear function. This linear function is defined as $(a_3x+b_3)$. Notice that within this correlation model, P1(x) and P4(x) are not limited to being linear functions and are free to be non-linear functions to better fit contrast sensitivity data. However, this model does require that the difference in the logarithm of P1(x) and logarithm of P4(x) be expressed as a linear function.

In some embodiments, the coefficients a1, b1, a2, b2, a3 and b3 are computed using a TICAP data fit algorithm ITCAPDFA 512 selected as the Newton-Raphson algorithm [1] by fitting the above defined correlation model (P1(x) through P4(x) probability equations) to the contrast sensitivity data. The CST (x) values are plotted with respect to a first probability (P) axis and with respect to a second (x) value axis, where the first axis and second axis are orthogonal to each other. CST parameter (x) values that are known to be associated with subjects known to be clinically assigned to a particular health classification are plotted to have a probability of 1 of being associated with a subject (viewer) assigned to that particular health classification, and other (x) values for that CST parameter are plotted to have an associated probability of 0 for being associated with a subject that is clinically assigned to that particular health classification.

For example, CST parameter (x) values that are known to be associated with subjects known to be clinically diagnosed as having Alzheimer's disease are assigned a probability of 1 for being associated with a subject that is clinically diagnosed as having Alzheimer's disease, while all other (x) values for that CST parameter are plotted to have an associated probability of 0 for being associated with a subject that is clinically diagnosed as having Alzheimer's disease.

In one embodiment, an implementation of such a best fit algorithm can be performed by a Matlab function, called mnrfit( ), to estimate the values of the coefficients. The mnrfit( ) function iteratively determines the coefficients (a1, b1, a2, b2, a3 and b3) that best fit a set of contrast sensitivity data in combination with actual clinical health classification information of each subject associated with the contrast sensitivity data.

For example, hypothetically, if subject number 0234 was clinically diagnosed with Alzheimer's disease and has an associated RightDurationTime CST parameter value of 350 seconds, then the HCAPPA coefficient generator, via the HCAP Data Fit algorithm (HCAPDFA) 512, factors this unit of data, along with other units of sample data, to determine the values of the coefficients (a1, b1, a2, b2, a3, and b3) that best fit the combination of both the correlation model defined with equations P1(x), P2(x), P3(x) and P4(x) and available contrast sensitivity test result data.

Once these HCAPPA coefficients are determined, the HCAPPA and the coefficients incorporated into the HCAPPA are employed to process the CST output file 412 of a new subject (viewer) 140 not having any known associated clinical health classification. The HCAPPA outputs a set of probabilistic health classifications which predict what clinical health classification(s) the subject (viewer) 140 would likely be appropriately assigned to, if clinically evaluated.

For example, a new subject would have no known prior testing with respect to Alzheimer's disease (AD), Mild Cognitive Impairment (MCI) or Cognitive Complaint (CC), but would have associated contrast sensitivity (CS) test result data. From this CS test data, a set of probabilistic health classifications can be determined for that new subject with respect to Normal Health, Alzheimer's disease, Mild Cognitive Impairment or Cognitive Complaint based upon a correlation model as described herein.

Each of the equations (4) through (7) operate as a portion of the health correlation assessment procedure predictive algorithm (HCAPPA). Equation (4) determines the probability of appropriately classifying a subject as having clinical Normal Health (NH) based upon the contrast sensitivity test result data for that subject. Equation (5) determines the probability of appropriately classifying a subject as having clinical Cognitive Complaint(s) based upon the contrast sensitivity test result data for that subject. Equation (6) determines the probability of appropriately classifying a subject as having clinical Mild Cognitive Impairment (MCI) based upon the contrast sensitivity test result data for that subject. Equation (7) determines the probability of appropriately classifying a subject as having clinical Alzheimer's Disease based upon the contrast sensitivity test result data for that subject.

FIG. 6B illustrates a representation of the types of data input, processed and generated by the health correlation assessment procedure 470 HCAP. Each subject is identified by a unique identifier 612, has associated personal attributes 614, associated contrast sensitivity test results 616. The aforementioned data is obtained from CST output file 412 and optionally another source of supplemental data, such as supplemental personal attribute data.

In response to input and processing of data 612-616, the HCAP 470, employing a selected predictive algorithm (HCAPPA) 424 generates outputs a set of one or more probabilistic health classifications 618 in accordance with equations (4) through (7) of FIG. 6A. As shown, (4) probabilistic health classifications are listed for each subject. For a first subject (Number 0395012), a set of probabilistic health classifications include Alzheimer's Disease (AD) having a probability equal to (53%), mild cognitive impairment (MCI) equal to (28%), cognitive complaint(s) (%15) and normal health (4%).

Note that these probabilistic health classifications are not actual health classifications 518 listed in FIG. 5B). For example, hypothetically, if first subject (Number 0395012) received clinical testing and evaluation, this first subject may be actually and clinically classified as MCI, despite the HCAP predicting that AD is most probable. However, use of another algorithm by the HCAP 470, or use of the same algorithm with other coefficients that are generated based upon a larger and or more diverse repository of sample data, may yield a more accurate prediction that MCI is the most likely appropriate health classification.

Figure 7A:
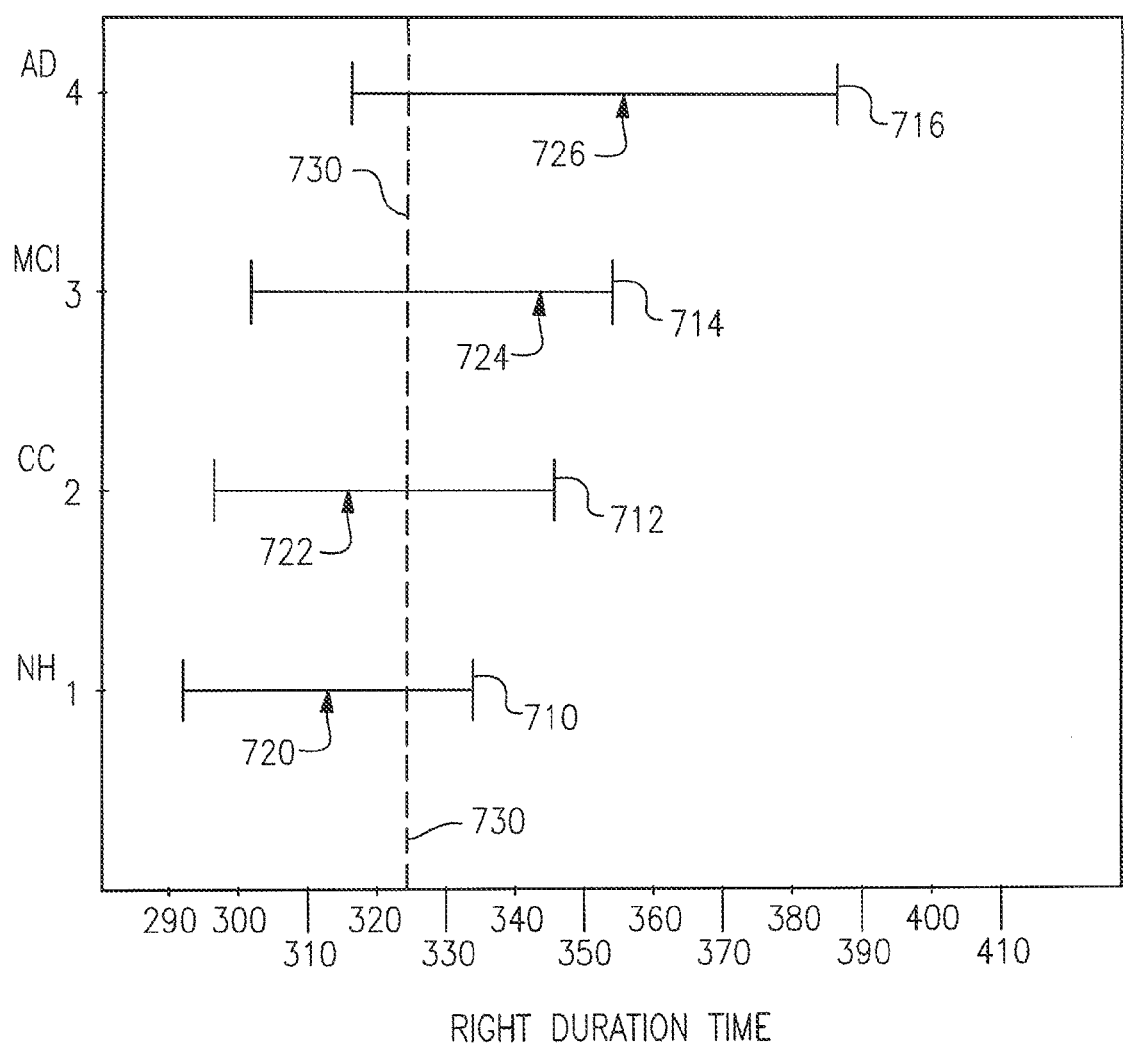
FIGS. 7A-7C illustrate sample data representing a RightDurationTime and PeripheralRight contrast sensitivity test (CST) parameter measurements and an age personal attribute with respect to sample subjects assigned within (4) actual clinical health classifications.

FIG. 7A illustrates ranges of sample data representing a RightDurationTime values with respect to (83) subjects assigned to (4) clinical health classifications. The RightDurationTime is defined as the elapsed time required to complete a contrast sensitivity test for the right eye of one subject. This data, also referred to herein as sample data, is acquired as a portion of a contrast sensitivity test result for each of the (83) subjects, also referred to herein as sample subjects. The contrast sensitivity test result data for each of the (83) sample subjects, can be represented in other ways, including for example, represented as a two dimensional distribution, a chi-squared distribution and/or measured via mean and/or median values, standard deviation values etc.

The sample data includes (29) sample subjects clinically classified being of Normal Health (NH), (18) sample subjects classified as having Cognitive Complaints (CC), (27) sample subjects classified as having mild cognitive impairment (MCI) and (9) sample subjects classified as having Alzheimer's disease. This sample data is processed to determine the health classification assessment algorithm (HCAA) parameters (a1, b1, a2, b2, a3, b3, a4 and b4) using a best fit algorithm employing the equations (0) through (3) of FIG. 6A.

As shown, a value of the Right Duration Time measurement of subjects having Normal Health (NH), have a range 710 between 291-333 seconds and have a mean 720 of approximately 312 seconds. The RightDurationTime measurement for subjects having cognitive complaints (CC) have a range 712 between 297-346 seconds and have a mean 722 of approximately 321.5 seconds. The RightDurationTime measurement for subjects having mild cognitive impairment (MCI) have a range 714 between 303-355 seconds and have a mean 724 of approximately 329 seconds. The RightDurationTime measurement for subjects having Alzheimer's disease have a range 716 between 315-384 seconds and have a mean 726 of approximately 349.5 for subjects having Alzheimer's disease.

A shown, the sample subjects that are clinically classified as actually having Alzheimer's Disease (AD) typically, require more RightDurationTime on average than that of subjects that are classified as actually having Mild Cognitive Impairment (MCI), who typically require more RightDurationTime on average than subjects that are clinically classified as actually having Cognitive Complaint(s), who typically require more RightDurationTime on average than subjects that are clinically classified as actually having Normal Health (NH).

Despite the above observation, there is much overlap, and hence ambiguity, when interpreting this data with the naked eye. A new subject requiring a RightDurationTime of between 300 and 340 seconds falls within at least (3) different health classifications. Also for example, a hypothetical subject requiring a RightDurationTime value 730 of 325 seconds (falls within the range of sample data for all (4) clinical health classifications. Many other hypothetical RightDurationTime values tall within the range of at least (2) clinical health classifications. As a result, despite any perceived visual correlation, quantifying an accurate correlation between the RightDurationTime and appropriate assignment to one of (4) clinical health classifications is not clear from observation alone with respect to this sample data.

Figure 7B:
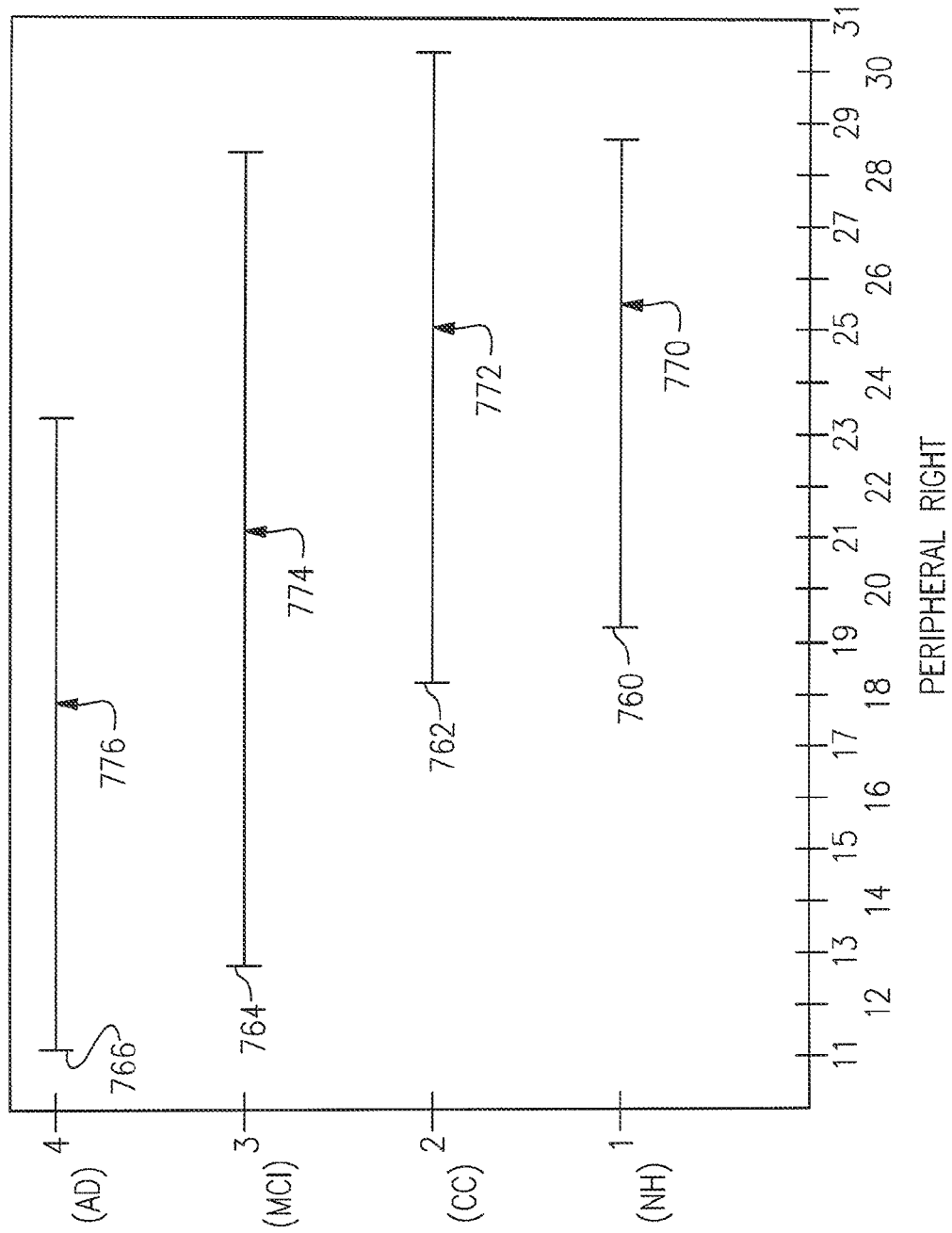

FIG. 7B illustrates ranges of sample data representing PeripheryRightEye contrast sensitivity measurement values with respect to the (83) sample subjects that are each assigned to (4) clinical health classifications. The PeripheryRightEye measurement is defined as the average of contrast sensitivity thresholds of (38) retinal zones that are located within the periphery area of the right eye (See FIGS. 3A-3B). The PeripheryRightEye data for each of the (83) sample subjects, can be represented in other ways, including for example, represented as a two dimensional distribution, a chi-squared distribution and/or measured via mean and/or median values, standard deviation values etc.

The sample data includes (29) sample subjects clinically classified being of Normal Health (NH), (18) sample subjects classified as having Cognitive Complaints (CC), (27) sample subjects classified as having mild cognitive impairment (MCI) and (9) sample subjects classified as having Alzheimer's disease. This sample data is processed to determine the health classification assessment algorithm (HCAA) parameters (a1, b1, a2, b2, a3 and b3) using a best fit algorithm employing the equations (0) through (3) of FIG. 6A.

As shown, a value of the PeripheryRightEye measurement of subjects having Normal Health (NH), have a range 760 between 19.28-28.73 dB and have a mean 770 of approximately 24.00. The PeripheryRightEye measurement for subjects having cognitive complaints (CC) have a range 762 between 18.21-30.23 dB and have a mean 772 of approximately 24.22. The PeripheryRightEye measurement for subjects having mild cognitive impairment (MCI) have a range 764 between 12.86-28.31 dB and have a mean 774 of approximately 20.59 dB. The PeripheryRightEye measurement for subjects having Alzheimer's disease have a range 766 between 11.55-23.31 and have a mean 776 of approximately 17.43 dB for subjects having Alzheimer's disease.

A shown, the sample subjects that are clinically classified as actually having Alzheimer's Disease (AD), have a lower average PeripheryRightEye CST parameter value than that of subjects that are classified as actually having Mild Cognitive Impairment (MCI), who have a lower average PeripheryRightEye CST parameter value than sample subjects that are clinically classified as actually having Cognitive Complaint(s), who have approximately the same average PeripheryRightEye CST parameter as sample subjects that are clinically classified as actually having Normal Health (NH).

Despite the above observations, there is much overlap and uncertainty, when visually interpreting this sample data in relation with the (4) clinical health classifications. For example, a new subject having a PeripheryRightEye value of between 18.3 and 23.3 dB falls within (3) different health classifications within the sample data. Also for example, a hypothetical subject having a PeripheryRightEye value 780 of 21 dB, falls within all (4) clinical health classifications. Many other hypothetical PeripheryRightEye values fall within the range of at least (2) clinical health classifications. As a result, despite any perceived visual correlation, accurately quantifying a correlation between any PeripheryRightEye contrast sensitivity measurement from this sample data and appropriate assignment to one of (4) clinical health classifications is not clear from visual observation alone.

Figure 7C:
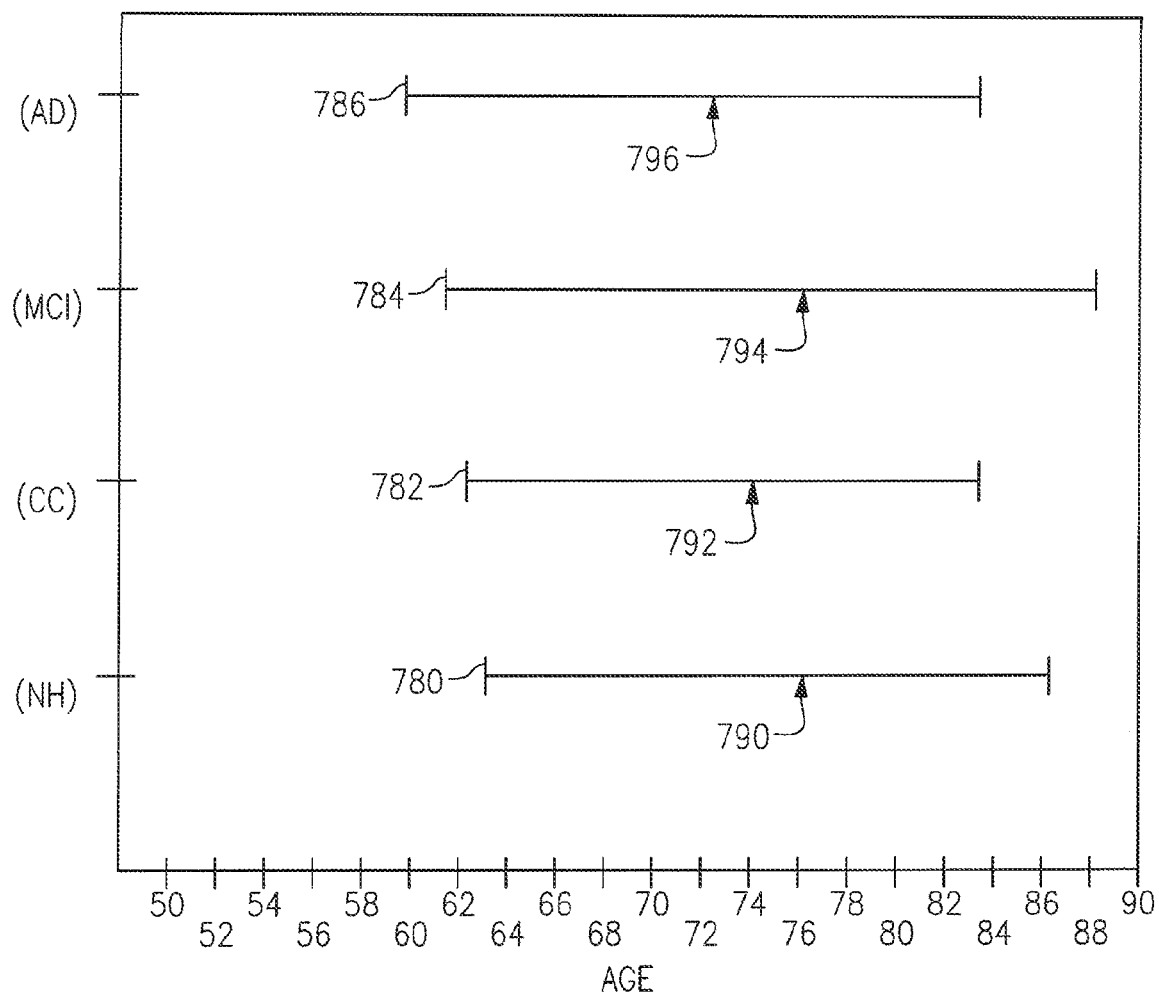

FIG. 7C illustrates ranges of sample data representing an age personal attribute with respect to the (83) sample subjects that are each assigned to (4) clinical health classifications. This age parameter is technically a non-contrast sensitivity test (non-CST) parameter. However, the age of a test taking subject can be extracted from a Zeiss FDT output file 412 in the same automated fashion of a CST parameter.

The sample data includes (29) sample subjects clinically classified being of Normal Health (NH), (18) sample subjects classified as having Cognitive Complaints (CC), (27) sample subjects classified as having mild cognitive impairment (MCI) and (9) sample subjects classified as having Alzheimer's disease. This sample data is processed to determine the health classification assessment algorithm (HCAA) parameters (a1, b1, a2, b2, a3 and b3) using a best fit algorithm employing the equations (0) through (3) of FIG. 6A.

As shown, a value of the age of subjects having Normal Health (NH), have a range 780 between 63-86 years of age and have a mean 770 of approximately 74.5 years. The age for subjects having cognitive complaints (CC) have a range 782 between 62-83 years of age and have a mean 792 of approximately 72.5 years. The age for subjects having mild cognitive impairment (MCI) have a range 784 between 61-88 years and have a mean 794 of approximately 74.5 years. The age for subjects having Alzheimer's disease have a range 786 between 60-83 years of age and have a mean 796 of approximately 71.5 years for subjects having Alzheimer's disease.

As shown, the sample subjects that are clinically classified as actually having Alzheimer's Disease (AD), have an age range that is approximate to that of subjects that are classified as actually having Mild Cognitive Impairment (MCI), who have an age range that is approximate to that of subjects that are clinically classified as actually having Cognitive Complaint(s), who have an age range that is approximate to that of average sample subjects that are clinically classified as actually having Normal Health (NH). As a result, there does not appear to be much of any visual correlation, between the age of the CST performing subject and their appropriate assignment to one of (4) clinical health classifications.

However, a combining and plotting values one or more individual a CST parameters, with the age value for each of the CST performing subjects, may reveal a mathematical significant correlation between the combination of CST parameters and age, for each particular subject, that can be quantified and exploited within an accordingly designed embodiment of a HCAPPA algorithm.

Figure 8A:
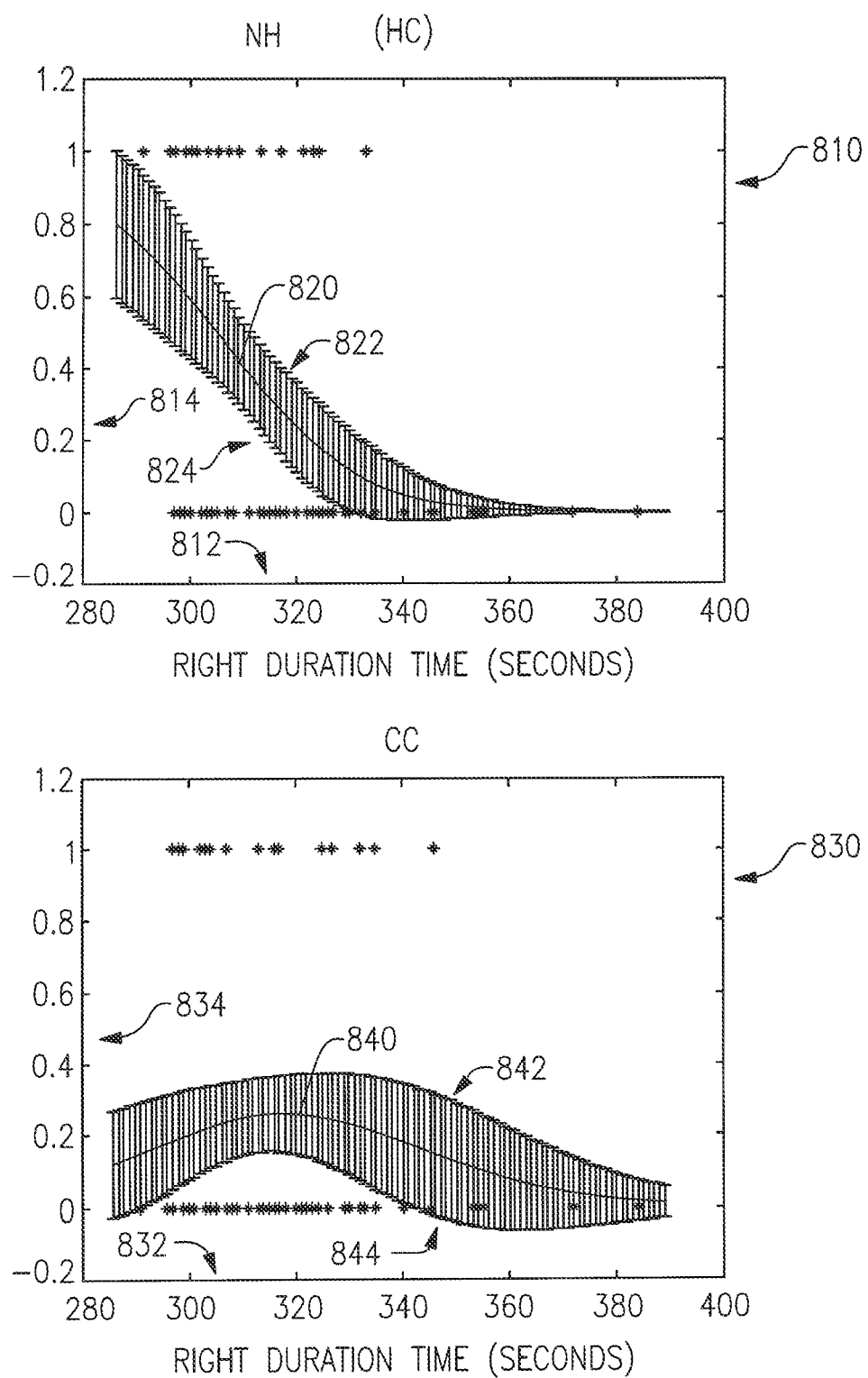
FIGS. 8A-8C illustrate graphs of a correlation model probability of a subject's being appropriately classified as having one of four health classifications as a function of a RightDurationTime parameter value obtained from eye contrast sensitivity test result.
Figure 8B:
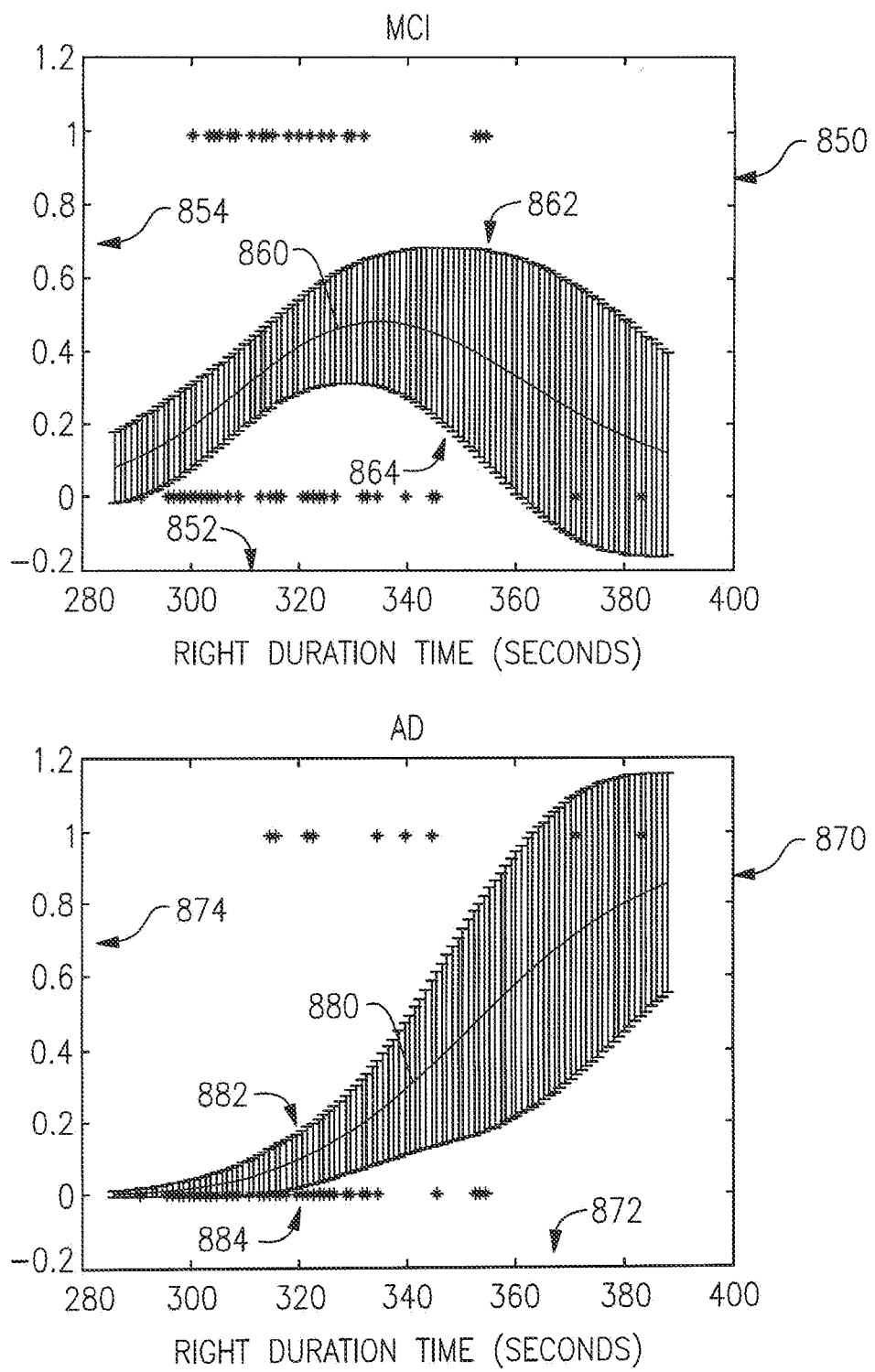
Figure 8C:
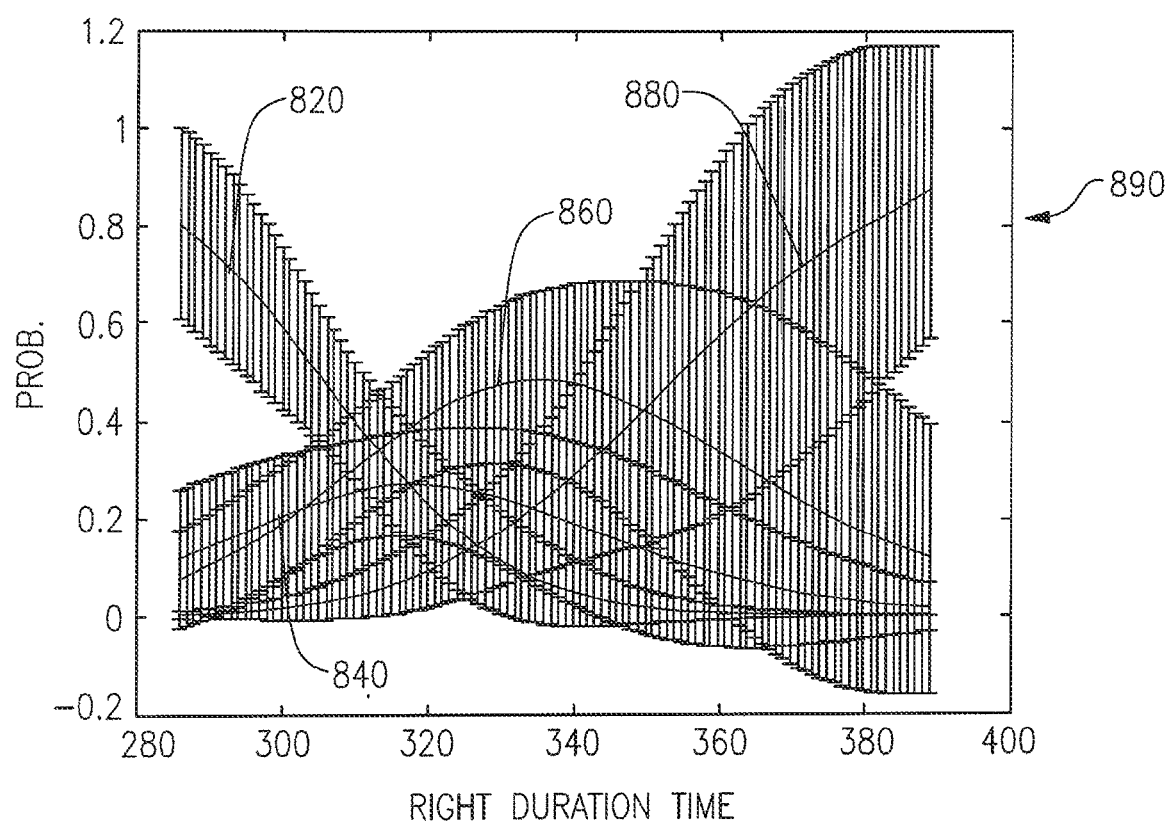

FIGS. 8A-8C illustrate graphs of a probability of a subject's being appropriately classified as having one of four health classifications as a function of a RightDurationTime contrast sensitivity test parameter value.

FIG. 8A illustrates a graph 810 of a probability (P1) of a subject (viewer) being appropriately assigned to a normal health (NH) classification (having normal health in accordance with a clinical standard) as a function of a RightDurationTime CST parameter value. This graph 810 is computed in accordance with the correlation model equation (4) of FIG. 6A and sample data of (83) subjects The center line 820 is a function representing a computed probability, indicated on a vertical axis 814 of the graph 810, of a subject appropriately being clinically classified as having Normal Health, also referred to here as a healthy control (HC) subject.

This computed probability 820 is a function of a RightDurationTime value received by a subject and indicated on a horizontal axis 812 of the graph 810. The error bars vertically spanning across the center line 820 indicate a 95% confidence range for each probability value located along an intersection with the center line 820. In other words, based upon this mathematical model and its assumptions, there is 95% confidence that the actual probability for each RightDurationTime CST value indicated along axis 812, falls within the probability range indicated by an upper limit 822 and a lower limit 824 of the error bars vertically spanning across the center line 820.

The coefficient values for (a1, a2, a3) that are computed based upon the above described best fit algorithm and the RightDurationTime sample data are (−0.135, −0.076, −0.050). The coefficient values for (b1, b2, b3) that are computed based upon the above described best fit algorithm and the sample data are (44.330, 25.469, 17.644). Incorporating these aforementioned coefficient values into equation (4) of FIG. 6A yields the graph of probability (P1) shown here.

Graph 830 is of a probability ($P_2$) of a subject (viewer) being appropriately assigned to a cognitive complaint (CC) classification (having cognitive complaints assessed in accordance with a clinical standard) as a function of a RightDurationTime CST parameter value. This graph is computed in accordance with the correlation model equation (5) of FIG.

6A and sample data of (83) subjects The center line 840 is a function representing a computed probability, indicated on a vertical axis 834 of the graph 830, of a subject appropriately being clinically classified as having Cognitive Complaints.

This computed probability 840 is a function of a RightDurationTime value received by a subject and indicated on a horizontal axis 832 of the graph 830. The error bars vertically spanning across the center line 840 indicate a 95% confidence range for each probability value located along an intersection with the center line 840. In other words, based upon this mathematical model and its assumptions, there is 95% confidence that the actual probability for each RightDurationTime CST value indicated along axis 812, falls within the probability range indicated by an upper limit 842 and a lower limit 844 of the error bars vertically spanning across the center line 840.

FIG. 8B illustrates a graph 850 of a probability (P3) of a subject (viewer) being appropriately assigned to a mild cognitive impairment (MCI) health classification (assigned in accordance with a clinical standard) as a function of a RightDurationTime CST parameter value. This graph 850 is computed in accordance with the correlation model equation (6) of FIG. 6A and sample data of (83) subjects The center line 860 is a function representing a computed probability, indicated on a vertical axis 854 of the graph 860, of a subject appropriately being clinically classified as having Mild Cognitive Impairment (MCI).

This computed probability 860 is a function of a RightDurationTime value received by a subject and indicated on a horizontal axis 852 of the graph 850. The error bars vertically spanning across the center line 860 indicate a 95% confidence range for each probability value located along an intersection with the center line 860. In other words, based upon this mathematical model and its assumptions, there is 95% confidence that the actual probability for each RightDurationTime CST value indicated along axis 852, falls within the probability range indicated by an upper limit 882 and a lower limit 864 of the error bars vertically spanning across the center line 860.

Graph 870 is of a probability ($P_4$) of a subject (viewer) being appropriately assigned to an Alzheimer's Disease (AD) health classification (assigned in accordance with a clinical standard) as a function of a RightDurationTime CST parameter value. This graph 870 is computed in accordance with the correlation model equation (7) of FIG. 6A and sample data of (83) subjects The center line 880 is a function representing a computed probability, indicated on a vertical axis 884 of the graph 870, of a subject appropriately being clinically classified as having Alzheimer's Disease (AD).

This computed probability 880 is a function of a RightDurationTime value received by a subject and indicated on a horizontal axis 872 of the graph 870. The error bars vertically spanning across the center line 880 indicate a 95% confidence range for each probability value located along an intersection with the center line 880. In other words, based upon this mathematical model and its assumptions, there is 95% confidence that the actual probability for each RightDurationTime CST value indicated along horizontal axis 872, fills within the probability range indicated by an upper limit 882 and a lower limit 884 of the error bars vertically spanning across the center line 880.

FIG. 8C illustrates a graph 890 of probabilities (P1, P2, P3, P4) of FIGS. 8A-8B superimposed onto one graph 890.

FIG. 9 is a matrix illustrating a relationship between the results of the predicted and actual health classifications based upon a single CST (RightDurationTime) parameter value. As shown, (46 of 83) subjects (i.e. 26+11+8+1=46) are predicted as more likely of being clinically classified as having normal health than likely of being clinically classified within the CC, MCI or Alzheimer's disease classifications. Also, (0 of 83) subjects are predicted to be more likely of being clinically classified as having cognitive complaints (CC) than likely of being clinically classified as not having cognitive complaints. Also, (34 of 83) subjects (i.e. 3+7+17+7) are predicted as more likely of being clinically classified as having mild cognitive impairment (MCI) than likely of being clinically classified as not having mild cognitive impairment (MCI). Also, (3 of 83) subjects (i.e. 2+1) are predicted as more likely of being clinically classified as having Alzheimer's disease than likely of being clinically classified as not having Alzheimer's disease.

From this analysis (26 of 29) subjects that are of actual (clinical) normal health, are predicted as having normal health, and (7 of 18) subjects actually having (clinical) cognitive complaints, are predicted as having cognitive complaints, and (17 of 27) subjects actually having mild cognitive impairment (MCI) are predicted as having mild cognitive impairment (MCI) and finally, only (1 of 9) sample subjects actually having clinical Alzheimer's Disease (AD) are predicted as having Alzheimer's Disease (AD).

The sensitivity of normal health (NH) prediction is (26/29) 89.6%, the sensitivity of the cognitive complaint (CC) prediction is (0/18) 0%, the sensitivity of the mild cognitive impairment (MCI) prediction is (17/27) 62.9%, the sensitivity of the AD prediction is (1/9) 11.1%. Note that the sensitivity of the combination of MCI plus AD is (27/36) 75%. The sensitivity of the combination of CC, MCI plus AD is (34/54)=62.9%.

What the aforementioned sensitivity values indicate is that this particular RightDurationTime single CST parameter correlation model is highly sensitive to subjects having actual normal health, but is insensitive to subjects with cognitive complaints (CC), somewhat sensitive to subjects having actual clinical Mild Cognitive Impairments and much less sensitive to subjects having actual clinical Alzheimer's disease. However, there is substantial sensitivity (75%) for the combination of MCI and AD, which is arguably a combination of Alzheimer's Disease and pre-Alzheimer's Disease health classifications.

It is desired that this correlation model evolve to achieve higher sensitivity for clinically verifiable CC, MCI and AD so that fewer subjects in these clinically verifiable categories are not recognized by the HCAPPA. This is desired, even if it comes that the cost of lower NH sensitivity, given that the cost penalty for not recognizing normal health is advising and performing an unnecessary Alzheimers disease related clinical test. Conversely, the cost penalty for not recognizing an Alzheimer's related disease classification can be unnecessary progression of the Alzheimer's disease within early treatment, which could be much more costly.

FIG. 10 illustrates a multiple CST parameter correlation model and correlation assessment procedure predictive algorithm (HCAPPA). In this second embodiment, like the first embodiment, P1 ($P_1$) represents a probability of a subject's being clinically classified as actually having Normal Health. P2 ($P_2$) represents a probability of a subject being clinically classified as actually having Cognitive Complaint(s) (CC). P3 ($P_3$) represents a probability of a subject's being clinically classified as actually having Mild Cognitive Impairment (MCI). P4 ($P_4$) represents a probability of a subject's being clinically classified as actually having Alzheimer's Disease. The Alzheimer's Disease classification includes mild, moderate, and severe sub-classifications of the Alzheimer's Disease in accordance with applicable standards associated with the Alzheimer's Disease Association.

Unlike the first embodiment of the HCAPPA, the above (4) probabilities (P1, P2, P3 and P4) are each a function of multiple (5) selected CST parameters, represented by the variables (x1, x2, x3, x4 and x5). These CST parameters are RightDurationTime (x1), PeriCenRatioRightEye (x2), SupInfRatioRightEye (x3), MacularArcRightEye (x4) and SuperiorQuadRatioRightEye (x5).

As shown, the PeriCenRatioRightEye CST parameter (x2) is a function of the PeripheryRightEye and CentralRightEye CST parameters. The SupInfRatioRightEye (x3) CST parameter is a function of the SuperiorRightEye and InferiorRightEye CST parameters. The SuperiorQuadRatioRightEye (x5) CST parameter is a function of the SuperiorQuadRightEye1 and the SuperiorQuadRightEye2 CST parameters.

Like the first embodiment of the HCAPPA, Equation (0) indicates that P1+P2+P3+P4=1, meaning that for given set of CST parameter values of (x1, x2, x3, x4 and x5), the (4) probabilities sum to the value 1 and there is no overlap between the probabilities associated with each of the (4) health classifications. Each probability represents a predictive likelihood that a subject (viewer) 140 receiving a given set of CST parameter values (x1, x2, x3, x4 and x5), would be appropriately assigned to a particular health classification associated with that probability, based upon clinical test and measurements performed separately from the contrast sensitivity test (CST).

In accordance with this correlation model, a subject (viewer) 140 can be predictably assigned to health classifications of the set consisting of Normal Health, Cognitive Complaint. Mild Cognitive Impairment and Alzheimer's Disease. In response to an output of the HCAPPA, a health care practitioner may advise that the subject should seek clinical testing to verify that the subject should or should not be assigned to the classification in which the subject receives the highest predictive probability from the HCAP. However the subject may also have other smaller and predictive probabilities of being appropriately assigned to one or more other health classifications within this probabilistic set, for which clinical testing may also be advisable.

Equation (11) indicates that the logarithm of the ratio of P2 (x1, x2, x3, x4, x5) divided by P1 (x1, x2, x3, x4, x5), which is equivalent to the logarithm of P2 (x1, x2, x3, x4, x5) minus the logarithm of P1 (x1, x2, x3, x4, x5), is expressed as a linear function. This linear function is defined as $(a_{11}x_1 + a_{12}x_2 + a_{13}x_3 + a_{14}x_4 + a_{15}x_5 + b_1)$. Notice that within this correlation model, P1(x) and P2(x) are not limited to being linear functions and are free to be non-linear functions to better fit contrast sensitivity data. However, this model does require that the difference in the logarithm of P1(x) and logarithm of P2(x) be expressed as a linear function.

Equation (2) indicates that the logarithm of the ratio of P3(x) divided by P1(x), which is equivalent to the logarithm of P3(x) minus the logarithm of P1(x), is expressed as a linear function. This linear function is defined as $(a_{11}x_1 + a_{22}x_2 + a_{23}x_3 + a_{24}x_4 + a_{25}x_5 + b_2)$ Notice that within this correlation model, P1(x) and P3(x) are not limited to being linear functions and are free to be non-linear functions to better fit contrast sensitivity data. However, this model does require that the difference in the logarithm of P1(x) and logarithm of P3(x) be expressed as a linear function.

Equation (3) indicates that the logarithm of the ratio of P4(x) divided by P1(x), which is equivalent to the logarithm of P4(x) minus the logarithm of P1(x), is expressed as a linear function. This linear function is defined as $(a_{31}x_1 + a_{32}x_2 + a_{33}x_3 + a_{34}x_4 + a_{35}x_5 + b_3)$ Notice that within this correlation model, P1(x) and P4(x) are not limited to being linear functions and are free to be non-linear functions to better fit contrast sensitivity data. However, this model does require that the difference in the logarithm of P1(x) and logarithm of P4(x) be expressed as a linear function.

The coefficients $(a_{11}, a_{12}, a_{13}, a_{14}, a_{15})$, $(a_{21}, a_{22}, a_{23}, a_{24}, a_{25})$, $(a_{31}, a_{32}, a_{33}, a_{34}, a_{35})$ and $(b_1, b_2, b_3)$ are computed using Newton-Raphson algorithm [1] by fitting the above defined correlation model to the contrast sensitivity data. The CST $(x_1, x_2, x_3, x_4, x_5)$ values are virtually plotted within a multi-dimensional space with respect to a first probability (P) axis. A set of CST parameter $(x_1, x_2, x_3, x_4, x_5)$ values that are known to be associated with a subject known to be clinically assigned to a particular health classification, are plotted as having a probability equal to 1 of being associated with a subject (viewer) assigned to that particular clinical health classification, and other sets of $(x_1, x_2, x_3, x_4, x_5)$ CST parameter values are virtually plotted to have an associated probability equal to 0 for being associated with a subject that is clinically assigned to that particular health classification.

For example, a set of CST parameter $(x_1, x_2, x_3, x_4, x_5)$ values that is known to be associated with a subject known to be clinically diagnosed as having Alzheimer's disease are assigned a probability of 1 for being associated with a subject that is clinically diagnosed as having Alzheimer's disease, while other sets of $(x_1, x_2, x_3, x_4, x_5)$ CST parameter values are virtually plotted to have an associated probability of 0, for being associated with a subject that is clinically diagnosed as having Alzheimer's disease.

In one embodiment, an implementation of such a best fit algorithm can be performed by a Matlab function, called mnrfit( ), to estimate the values of the coefficients $(a_{11}, a_{12}, a_{13}, a_{14}, a_{15})$, $(a_{21}, a_{22}, a_{23}, a_{24}, a_{25})$, $(a_{31}, a_{32}, a_{33}, a_{34}, a_{35})$ and $(b_1, b_2, b_3)$. The mnrfit( ) function iteratively determines the coefficients that best fit a set of sample contrast sensitivity data in combination with actual clinical health classification information of each subject associated with the contrast sensitivity data.

Once these HCAPPA coefficients are determined, the HCAPPA and the coefficients incorporated into the HCAPPA are employed to process the CST output file 412 of a new subject (viewer) 140 not having any known associated clinical health classification. The HCAPPA outputs a set of probabilistic health classifications which predict what clinical health classification(s) the subject (viewer) 140 would likely be appropriately assigned to, if clinically evaluated.

For example, a new subject would have no known prior testing with respect to Alzheimer's disease (AD), Mild Cognitive Impairment (MCI) or Cognitive Complaint (CC), but would have associated contrast sensitivity (CS) test result data. From this CS test data, a set of probabilistic health classifications can be determined for that new subject with respect to Normal Health, Alzheimer's disease, Mild Cognitive Impairment or Cognitive Complaint based upon a correlation model as described herein.

Each of the equations (14) through (17) operate as a portion of the health correlation assessment algorithm (HCAPPA). Equation (14) determines the probability of appropriately classifying a subject as having clinical Normal Health (NH) based upon the contrast sensitivity test result data for that subject. Equation (15) determines the probability of appropriately classifying a subject as having clinical Cognitive Complaint(s) based upon the contrast sensitivity test result data for that subject. Equation (16) determines the probability of appropriately classifying a subject as having clinical Mild Cognitive Impairment (MCI) based upon the contrast sensitivity test result data for that subject. Equation (17) determines the probability of appropriately classifying a subject as having clinical Alzheimer's Disease based upon the contrast sensitivity test result data for that subject.

FIG. 11 is a matrix illustrating a relationship between the results of the predicted and actual health classifications based upon the multiple CST parameter correlation model of FIG. 10. As shown, (38 of 83) subjects (i.e. 24+8+6+0=38) are predicted as more likely of being clinically classified as having normal health than likely of being clinically classified as within the CC, MCI or Alzheimer's disease classifications. Also, (9 of 83) subjects are predicted to be more likely of being clinically classified as having cognitive complaints (CC) than likely of being clinically classified as not having cognitive complaints. Also, (31 of 83) subjects are predicted as more likely of being clinically classified as having mild cognitive impairment (MCI) than likely of being clinically classified as not having mild cognitive impairment (MCI). Also, (5 of 83) subjects are predicted as more likely of being clinically classified as having Alzheimer's disease than likely of being clinically classified as not having Alzheimer's disease.

From this analysis (24 of 29) subjects that are of actual (clinical) normal health (NH), are predicted as having normal health, and (4 of 18) subjects actually having (clinical) cognitive complaints (CC), are predicted as having cognitive complaints, and (18 of 27) subjects actually having mild cognitive impairment (MCI) are predicted as having mild cognitive impairment (MCI) and finally, only (4 of 9) sample subjects actually having clinical Alzheimer's Disease (AD) are predicted as having Alzheimer's Disease (AD).

The sensitivity of the normal health (NH) prediction is (24/29)=82.7%, the sensitivity of the cognitive complaint (CC) prediction is (4/18)=22.2%, the sensitivity of MCI is (17/27)=66.6%, and the sensitivity of Alzheimer's Disease (AD) prediction is (4/9)=55.5%. Importantly, the sensitivity of the MCI and AD classifications combined is 75% and the sensitivity of the CC, MCI and AD classifications (unhealthy classifications) combined is 83.3%.

Importantly, this multi-parameter embodiment provides substantially more sensitivity with respect to Alzheimer's Disease (11.1%→55.5%) and more sensitivity to the CC, MCI and AD classifications (non healthy classifications) combined (62.9%→83.3%).

It is desired that this correlation model evolve to achieve higher sensitivity for CC. MCI and AD so that fewer subjects in these categories are not recognized by the HCAPPA. This is desired, even if such improvement in sensitivity comes that the cost of lower specificity of normal health (NH), given that the cost penalty for not recognizing normal health is advising and performing an unnecessary Alzheimer's disease related clinical test. Conversely, the cost penalty for not recognizing an Alzheimer's related disease classification can be unnecessary progression of the Alzheimer's disease without early treatment, which could be much more costly in the long term.

The sensitivity of both the single and multi-parameter algorithms may further improve with access to more sample data. The sample data includes only (9 of 83) Alzheimer's Disease (AD) subjects. Access to more clinically identified AD subjects to improve the sensitivity and/or specificity either or both of these algorithms.

Figure 12:
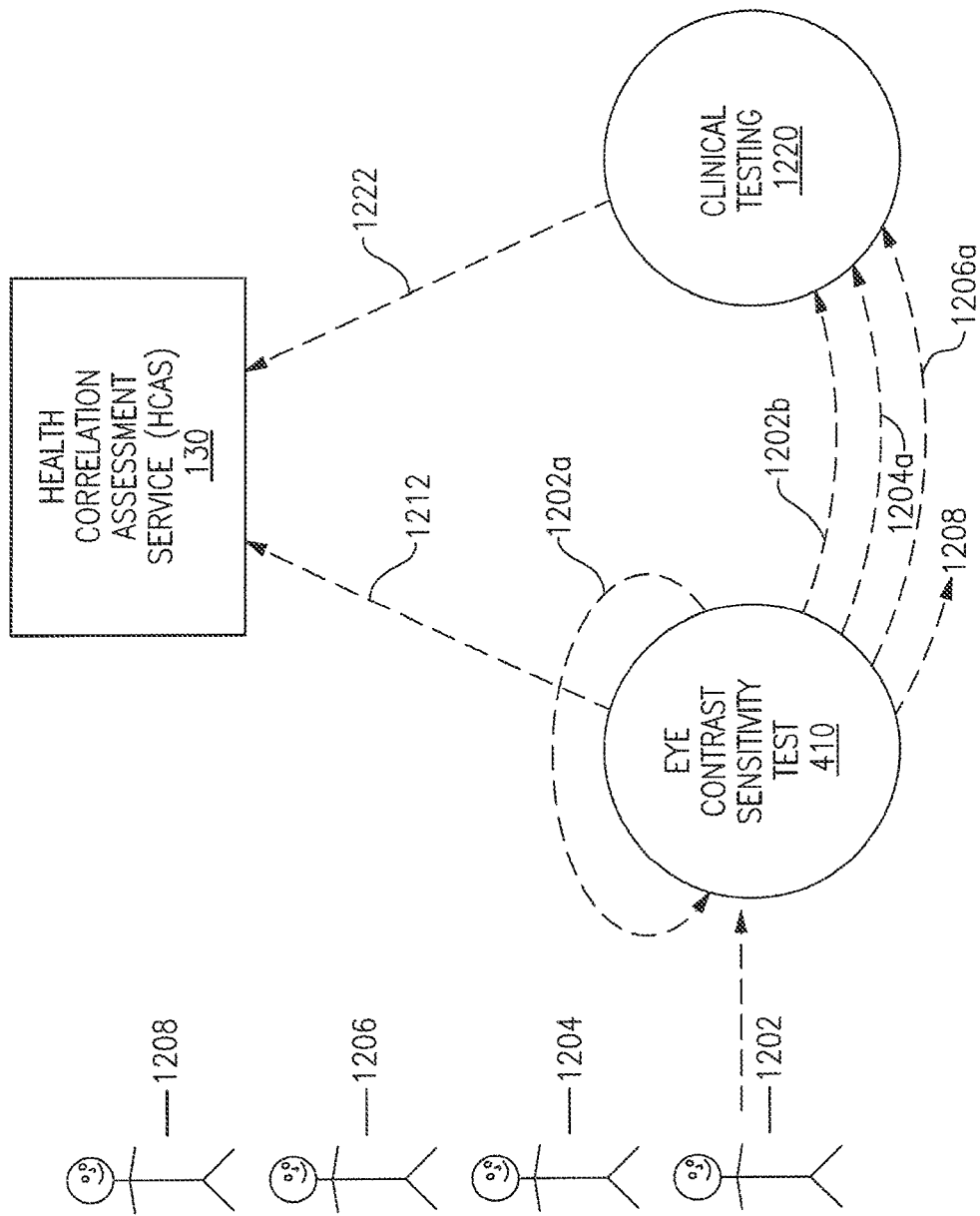
FIG. 12 illustrates systematic interoperation between contrast sensitivity testing, clinical testing and the health correlation assessment service.

FIG. 12 illustrates systematic interoperation among contrast sensitivity testing, clinical testing and the health correlation assessment service 130. As shown, a plurality of contrast sensitivity test taking subjects 1202-1206 receive contrast sensitivity testing 410.

The subject 1202 performs a first contrast sensitivity test (CST) 1202a which indicates normal health and performs a second CST 1202b (one year later) which indicates normal health, but that is significantly more likely of being classified as Mild Cognitive Impairment. After the second CST, subject 1202 elects to receive clinical testing 1220. Subject 1202 has an option of permitting a release of the HCS test(s) and the results of the clinical tests, to the health correlation assessment service (HCAS) 130.

A subject has an option to perform many test over time. Algorithms can be designed to quantity a chronological trend to measure effectiveness of medical treatment or possible progression of a disease or medical condition for which the CST is sensitive.

The subject 1204 performs a first contrast sensitivity test (CST) 1204a which indicates substantial likelihood of Mild Cognitive Impairment and a small likelihood of Alzheimer's disease and elects to receive clinical testing 1220. Clinical tests indicate Alzheimer's disease and subject 1204 elects to permit release of the contrast sensitivity tests and the clinical tests to the HCAS 130.

The subject 1206 performs a first contrast sensitivity test (CST) 1206a which indicates small likelihood of Mild Cognitive Impairment and elects to receive clinical testing 1220. Clinical tests indicate normal health and the subject 1206 elects to permit release of the contrast sensitivity tests and the clinical tests to the HCAS 130.

The subject 1208 performs a first contrast sensitivity test (CST) 1208a which indicates small likelihood of Mild Cognitive Impairment and elects not to receive clinical testing 1220. There are no clinical tests performed and subject 1208 elects to permit release of the contrast sensitivity tests to the HCAS 130 in case further contrast sensitivity testing and/or clinical testing is performed sometime in the future.

At the HCAS 130, specialists scrutinize data received for subjects from the CST 410 and clinical testing 1220 to decide for inclusion of the data received into the repository of sample data 550 managed within the HCAS 130. As a result, the repository of sample data 550 of the HCAS 130 and associated HCAP data fit algorithms (HCAPDFA) and HCAP predictive algorithms (HCAPPA) can be revised and enhanced over time to better exploit a larger and more representative set of sample Alzheimer's disease related data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for performing a probabilistic assessment for one or more Alzheimer's disease related clinical health classifications based upon results of a contrast sensitivity eye examination test, comprising:

an eye contrast sensitivity testing device that is configured to perform an eye contrast sensitivity test with respect to a first subject, and that is further configured to generate eye contrast sensitivity test result data, representing a result of said eye contrast sensitivity test with respect to said first subject;

a data access component for obtaining at least a portion of eye contrast sensitivity test result data from a first eye contrast sensitivity test performed by a first subject, from said eye contrast sensitivity testing device;

a health correlation assessment component that exercises a first algorithm in accordance with a correlation model, that includes exercise of a set of one or more mathematical equations that are each is applied to process said at least a portion of eye contrast sensitivity test result data of said first eye contrast sensitivity test, each of said first set of equations including a separate variable representing a numerical probability value associated with a separate probabilistic health classification, each said component outputs at least one numerical probability value representing an estimated probability of said first subject being clinically assigned into at least one of a plurality of Alzheimer's disease related health classifications, said health classifications including at least one classification indicating a presence of an Alzheimer's disease related abnormality within said first subject;

said first set of equations each employing a set of at least two mathematical coefficients, said coefficients each being a numerical value that is determined by exercise of a second algorithm configured for processing a repository of data in accordance with a correlation model, said repository of data including other eye contrast sensitivity test result data obtained from eye contrast sensitivity tests performed by subjects other than said first subject; and an output component that outputs information representing said probabilistic health classifications.

2. The apparatus of claim 1 wherein said first algorithm further accesses and processes personal attribute data associated with said first subject in combination with said eye contrast sensitivity test result data of said first eye contrast sensitivity test, to determine said probabilistic health classifications.

3. The apparatus of claim 1 wherein said probabilistic health classifications include one probability of a subject being appropriately classified as having a clinical stage of Alzheimer's disease.

4. The apparatus of claim 1 wherein said probabilistic health classifications include one probability of a subject being appropriately classified as having a pre-clinical or clinical stage of Alzheimer's disease.

5. The apparatus of claim 1 wherein said probabilistic health classifications include one probability of a subject being appropriately classified as having an absence of an Alzheimer's related disease.

6. The apparatus of claim 1 wherein said second algorithm inputs one of at least a personal attribute, such as age and gender and family history, in combination with a portion of a result of said contrast sensitivity test.

7. The apparatus of claim 1 wherein said at least a portion of a contrast sensitivity test result includes one contrast sensitivity test parameter, selected from at least one of RightDurationTime, PeripheryRightEye, CentralRightEye, SuperiorRightEye, InferiorRightEye, MacularArcRightEye and SuperiorQuadRightEye 1 and SuperiorQuadRightEye 2 contrast sensitivity test parameters.

8. The apparatus of claim 1 wherein said at least a portion of a contrast sensitivity test result includes measurements of more than one contrast sensitivity test parameter, selected from at least two of RightDurationTime, PeripheryRightEye, CentralRightEye, SuperiorRightEye, InferiorRightEye, MacularArcRightEye and SuperiorQuadRightEye 2 contrast sensitivity test parameters.

9. The apparatus of claim 1 wherein said at least a portion of a contrast sensitivity test result includes at least one contrast sensitivity test parameters including at least one of RightDurationTime, LeftDurationTime, MDLeftEye, MDRightEye, SuperiorLeftEye and SuperiorRight Eye.

10. A method for performing a probabilistic assessment for one or more Alzheimer's disease related clinical health classifications based upon results of a contrast sensitivity eye examination of a first subject, comprising the steps of:

providing an eye contrast sensitivity testing device that is configured to perform an eye contrast sensitivity test with respect to a first subject, and that is further configured to generate eye contrast sensitivity test result data, representing a result of said eye contrast sensitivity test with respect to said first subject;

obtaining at least a portion of an eye contrast sensitivity test result data for a first subject from said eye contrast sensitivity testing device;

exercising a first algorithm that includes exercise of a set of one or more mathematical equations, via a computer, circuitry, or one or more processors, that is applied to process said at least a portion of eye contrast sensitivity test result data, said first algorithm configured for determining a set of one or more probabilistic health classifications for said first subject, each of said equations including a separate variable representing a numerical probability value associated with a separate probabilistic health classification, each said numerical probability value representing an estimated probability of said first subject being clinically assigned into at least one Alzheimer's disease related clinical health classification, in accordance with a clinical evaluation of said first subject;

said first set of equations employing a set of at least two mathematical coefficients, said coefficients each being a numerical value that is determined by exercise of a second algorithm configured for processing a repository of data in accordance with a correlation model, said repository of data including eye contrast sensitivity test result data obtained from eye contrast sensitivity tests performed by subjects other than said first subject; and providing information representing said probabilistic health classifications.

11. The method of claim 10 wherein at least one said probabilistic health classifications include one classification of said first subject being appropriately classified as having a clinical or pre-clinical stage of Alzheimer's disease.

12. The method of claim 10 wherein said at least one probabilistic health classification includes one classification of a subject being appropriately classified as having an absence of Alzheimer's disease.

13. The method of claim 11 wherein said pre-clinical stage of Alzheimer's disease is at least one of mild cognitive impairment (MCI) and cognitive complaint (CC).

14. The method of claim 10 wherein said at least a portion of a contrast sensitivity test result includes one contrast sensitivity test parameter, selected from at least one of RightDurationTime, PeripheryRightEye, CentralRightEye, SuperiorRightEye, InferiorRightEye, MacularArcRightEye and SuperiorQuadRightEye 1 and SuperiorQuadRightEye 2 contrast sensitivity test parameters.

15. The method of claim 10 wherein said at least a portion of a contrast sensitivity test result includes at least one contrast sensitivity test parameters including at least one of RightDurationTime, LeftDurationTime, MDLeftEye, MDRightEye, SuperiorLeftEye and SuperiorRight Eye.

16. An system for performing an probabilistic assessment for one or more Alzheimer's disease related health classifications based upon results of a contrast sensitivity eye examination, comprising:

an eye contrast sensitivity testing device that is configured to perform an eye contrast sensitivity test with respect to a first subject, and that is further configured to generate eye contrast sensitivity test result data, representing a result of said eye contrast sensitivity test with respect to said first subject;

a data access component for obtaining at least a portion of a result of a contrast sensitivity test for a first subject, from said eye contrast sensitivity testing device;

a health correlation assessment procedure (HCAP) component that exercises a first algorithm, in accordance with a first correlation model, and that includes exercise of a set of one or more mathematical equations that are each applied to process at least a portion of a result of said eye contrast sensitivity test for said first subject, each of said equations including a separate variable representing a numerical probability value associated with a separate probabilistic health classification, each said numerical probability value representing an estimated probability of said first subject being clinically assigned into at least one Alzheimer's disease related health classification, based upon a clinical evaluation of said first subject;

said first set of equations each employing a set of at least two mathematical coefficients, said coefficients each being a numerical value that is determined by exercise of a second algorithm configured for processing a repository of data in accordance with a correlation model, said repository of data including eye contrast sensitivity test result data obtained from eye contrast sensitivity tests performed by subjects other than said first subject; and an output component that outputs information representing said probabilistic health classification.

17. The system of claim 16 wherein said first algorithm employs mathematical coefficients each having values that are periodically re-determined from re-processing of said repository of sample data, and wherein said repository of sample data evolves via periodic addition of said other eye contrast sensitivity test result data over time.

18. The system of claim 16 wherein said first algorithm further processes personal attribute data associated with said first subject, for determining a set of one or more probabilistic health classifications for said first subject.

19. The system of claim 16 wherein said HCAP component further provides information relating to prospect of whether said first subject would be appropriately assigned to one or more one non-Alzheimer's disease related health classifications including at least one of glaucoma, Parkinson's disease, Multiple Sclerosis, and head trauma.

20. The system of claim 16 wherein said HCAP component exercises a second algorithm that measures a change in contrast sensitivity test (CST) performance of said first subject over time for providing information relating to a prospect of whether said first subject would be appropriately assigned to one or more Alzheimer's or non-Alzheimer's disease related health classifications.

21. The system of claim 16 wherein said HCAP component exercises a third algorithm that measures a change in contrast sensitivity test (CST) performance of said first subject over time for measuring an effect of medical treatment applied to the first subject over time.

22. The apparatus of claim 1, wherein said correlation model is based, at least in part, upon an amount of time required for said test subject to complete said eye contrast sensitivity test.

23. The apparatus of claim 22, wherein said amount of time is obtained from said at least a portion of a contrast sensitivity test.

24. The apparatus of claim 1, wherein said correlation model is based, at least in part, upon an amount of time required for said test subject to complete said eye contrast sensitivity test.

25. The apparatus of claim 24, wherein said amount of time is obtained from said at least a portion of a contrast sensitivity test.

* * * * *